(12) United States Patent
Liu

(10) Patent No.: US 10,977,843 B2
(45) Date of Patent: Apr. 13, 2021

(54) SYSTEMS AND METHODS FOR DETERMINING PARAMETERS FOR MEDICAL IMAGE PROCESSING

(71) Applicant: SHANGHAI UNITED IMAGING HEALTHCARE CO., LTD., Shanghai (CN)

(72) Inventor: Yanyan Liu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 290 days.

(21) Appl. No.: 15/954,953

(22) Filed: Apr. 17, 2018

(65) Prior Publication Data

US 2019/0005686 A1 Jan. 3, 2019

(30) Foreign Application Priority Data

Jun. 28, 2017 (CN) .......................... 201710508324.X
Jun. 28, 2017 (CN) .......................... 201710508431.2
Jun. 30, 2017 (CN) .......................... 201710524197.2

(51) Int. Cl.
*G06T 11/00* (2006.01)
*G06N 3/04* (2006.01)
(Continued)

(52) U.S. Cl.
CPC .............. *G06T 11/008* (2013.01); *G06N 3/04* (2013.01); *G06N 3/08* (2013.01); *G06T 5/002* (2013.01);
(Continued)

(58) Field of Classification Search
None
See application file for complete search history.

(56) References Cited

U.S. PATENT DOCUMENTS 6,422,751 B1 7/2002 Aufrichtig et al.
6,682,491 B2 1/2004 Johnson
(Continued)

FOREIGN PATENT DOCUMENTS

CN 101336828 A 1/2009
CN 102768759 A 11/2012
(Continued)

OTHER PUBLICATIONS

Feng et al. Neural network CT image reconstruction method for small amount of projection data, Nuclear Instruments and Methods in Physics Research Section A: Accelerators, Spectrometers, Detectors etc., vol. 449, Issues 1-2, 2000, pp. 366-377, https://doi.org/10.1016/S0168-9002(99)01453-9 (Year: 2000).*
(Continued)

*Primary Examiner* — Tahmina N Ansari
(74) *Attorney, Agent, or Firm* — Metis IP LLC

(57) ABSTRACT

A system and method for determine a parameter for medical data processing are provided. The method may include obtaining sample data, the sample data may comprise at least one of projection data or a scanning parameter. The method may also include obtaining a first neural network model. The method may further include determining the parameter based on the sample data and the first neural network model. The parameter may comprise at least one of a correction coefficient or a noise reduction parameter.

25 Claims, 23 Drawing Sheets

(51) Int. Cl.
*G16H 30/40* (2018.01)
*G06N 3/08* (2006.01)
*G06T 5/00* (2006.01)
*G16H 30/20* (2018.01)
*G16H 40/63* (2018.01)

(52) U.S. Cl.
CPC ........... *G06T 11/005* (2013.01); *G16H 30/20* (2018.01); *G16H 30/40* (2018.01); *G16H 40/63* (2018.01); *G06T 2207/10081* (2013.01); *G06T 2207/20081* (2013.01); *G06T 2207/20084* (2013.01)

(56) References Cited

U.S. PATENT DOCUMENTS

| | | | |
|---|---|---|---|
| 10,607,099 B2* | 3/2020 | Cai | A61B 6/584 |
| 2005/0089215 A1 | 4/2005 | Staelin et al. | |
| 2005/0220265 A1 | 10/2005 | Besson | |
| 2006/0013353 A1 | 1/2006 | Hein | |
| 2013/0222430 A1 | 8/2013 | Bredno et al. | |
| 2014/0005971 A1 | 1/2014 | Roessl et al. | |
| 2015/0201895 A1* | 7/2015 | Suzuki | A61B 6/5211 382/131 |
| 2015/0279005 A1 | 10/2015 | Brendel et al. | |
| 2017/0143312 A1 | 5/2017 | Hedlund et al. | |
| 2019/0005686 A1* | 1/2019 | Liu | G06T 11/005 |
| 2019/0035116 A1* | 1/2019 | Xing | G06N 3/08 |
| 2019/0035118 A1* | 1/2019 | Zhao | G06T 5/50 |

FOREIGN PATENT DOCUMENTS

| | | | | |
|---|---|---|---|---|
| CN | 103961125 A | 8/2014 | | |
| CN | 105654434 A | 6/2016 | | |
| CN | 106327495 A | 1/2017 | | |
| CN | 106373109 A | 2/2017 | | |
| CN | 106600568 A | 4/2017 | | |
| CN | 106725569 A | 5/2017 | | |
| JP | H03102477 A | 4/1991 | | |
| WO | WO-2014036473 A1 * | 3/2014 | ........... A61B 6/5282 | |

OTHER PUBLICATIONS

First Office Action in Chinese Application No. 201710508431.2 dated Mar. 27, 2020, 9 pages.
First Office Action in Chinese Application No. 201710508324.X dated Mar. 2, 2020, 24 pages.
First Office Action in Chinese Application No. 201710524197.2 dated Mar. 31, 2020, 21 pages.

* cited by examiner

SYSTEMS AND METHODS FOR DETERMINING PARAMETERS FOR MEDICAL IMAGE PROCESSING

CROSS-REFERENCE TO RELATED APPLICATIONS

This application claims priority to Chinese Patent Application No. 201710508431.2, filed on Jun. 28, 2017, Chinese Patent Application No. 201710524197.2, filed on Jun. 30, 2017, and Chinese Patent Application No. 201710508324.X, filed on Jun. 28, 2017, the contents of which are incorporated herein by reference.

TECHNICAL FIELD

The present disclosure generally relates to systems and methods for processing projection data, and in particular, to systems and methods for correcting projection data.

BACKGROUND

Medical images, such as CT images, are important and necessary for medical diagnosis. A subject, such as a patient, may be scanned to obtain projection data which may be used to reconstruct an image of the subject. In some embodiments, due to influence of parameters of detector and/or environmental factors, artifacts and/or noise may exist in the reconstructed image of the subject. The artifacts and/or noise may reduce the quality of the reconstruction image and affect the subsequent processing, for example, lesion recognition and/or division. Hence, the projection data may need to be corrected for an accurate diagnosis. However, existing correction algorithms may take a long time to correct the projection data. Therefore, it is desirable to provide systems and methods for correcting projection data precisely and rapidly.

SUMMARY

According to an aspect of the present disclosure, a method for determining a parameter for medical image processing is provided. The method may include obtaining sample data, the sample data may comprise at least one of projection data or a scanning parameter. The method may also include obtaining a first neural network model. The method may further include determining the parameter based on the sample data and the first neural network model. The parameter may comprise at least one of a correction coefficient or a noise reduction parameter.

In some embodiments, the correction coefficient may be configured to correct an artifact relating to the projection data.

In some embodiments, the obtaining a first neural network model may comprise: generating an initial neural network model; obtaining first projection data of a subject corresponding to a plurality of scanning parameters, the first projection data of the subject being generated by scanning the subject with a scanner, and the plurality of scanning parameters relating to at least one of the scanner or the subject; generating second projection data of the subject based on the first projection data of the subject; training the initial neural network model with the first projection data and the second projection data to obtain the first neural network model.

In some embodiments, the subject may comprise a phantom.

In some embodiments, the generating second projection data of the subject based on the first projection data of the subject may comprise: reconstructing a first image of the subject from the first projection data of the subject; smoothing the first image of the subject to generate a second image of the subject; projecting the second image of the subject to generate the second projection data of the subject.

In some embodiments, the generating second projection data of the subject based on the first projection data of the subject may comprise: smoothing the first projection data of the subject to generate the second projection data.

In some embodiments, the generating second projection data of the subject based on the first projection data of the subject may comprise: reconstructing a first image of the subject from the first projection data of the subject; modelling the subject according to the first image; and calculating analytic equations of an X-ray transmission process to obtain the second projection data of the subject.

In some embodiments, the plurality of scanning parameters may comprise at least one of a tube voltage of the scanner or a tube current of the scanner.

In some embodiments, the optimization objective of the neural network training is that the desired correction coefficient is close to the known correction coefficient.

In some embodiments, the sample data may comprise third projection data relating to a subject, and the determining the parameter based on the sample data and the first neural network model may comprise: determining the correction coefficient based on the third projection data and the first neural network model, the third projection data being generated under the scanning parameter.

In some embodiments, the method further may comprise: correcting the third projection data based on the correction coefficient to generate corrected third projection data; reconstructing an image based on the corrected third projection data In some embodiments, the correcting the third projection data based on the correction coefficient to generate corrected third projection data may comprise: constructing a correction model based on the correction coefficient; generating the corrected third projection data based on the third projection data and the correction model.

In some embodiments, the correction model may comprise the first derivative of the detector response and/or the second derivative of the detector response.

In some embodiments, the correction coefficient may be configured to correct errors induced by a detector that collects the projection data.

In some embodiments, the sample data may comprise first projection data being generated by scanning air under the scanning parameter, and the determining a parameter based on the sample data and the first neural network model may comprise: determining the correction coefficient based on the first projection data and the first neural network model.

In some embodiments, the obtaining a first neural network model may comprise: generating an initial neural network model; obtaining a plurality of training samples, the plurality of training samples comprising at least one of a second scanning parameter or second projection data, the second projection data being generated by scanning air under the second scanning parameter; training the initial neural network model with the at least one of the second scanning parameter or the second projection data to obtain the first neural network model.

In some embodiments, the obtaining a first neural network model may comprise: generating an initial neural network model; obtaining training projection data and noise distribution of the training projection data; training the initial neural network model with the training projection data and the noise distribution of the training projection data to obtain the first neural network model.

In some embodiments, the method further may comprise: performing a noise reduction operation on the projection data based on the parameter, the parameter being a noise reduction parameter.

In some embodiments, the noise reduction parameter may comprise spectrum parameter of the noise distribution, the thresholds of each layer of the wavelet decomposition, regularization term coefficients of the total variation of minimize data.

According to another aspect of the present disclosure, a system for determining a parameter for medical data processing may include at least one computer-readable storage medium including a set of instructions and at least one processor in communication with the at least one computer-readable storage medium. When executing the instructions, the at least one processor is directed to: obtain sample data, the sample data comprising at least one of projection data or a scanning parameter; obtain a first neural network model; determine the parameter based on the sample data and the first neural network model, the parameter comprising at least one of a correction coefficient or a noise reduction parameter.

In some embodiments, the correction coefficient may be configured to correct an artifact relating to the projection data.

In some embodiments, the at least one processor is further configured to: obtain first projection data of a subject corresponding to a plurality of scanning parameters, the first projection data of the subject being generated by scanning the subject with a scanner, and the plurality of scanning parameters relating to at least one of the scanner or the subject; generate second projection data of the subject based on the first projection data of the subject; train the initial neural network model with the first projection data and the second projection data to obtain the first neural network model.

In some embodiments, the at least one processor is further configured to: reconstruct a first image of the subject from the first projection data of the subject; smooth the first image of the subject to generate a second image of the subject; project the second image of the subject to generate the second projection data of the subject.

In some embodiments, to generate the second projection data of the subject based on the first projection data of the subject, the at least one processor is configured to: reconstruct a first image of the subject from the first projection data of the subject; model the subject according to the first image; and calculate analytic equations of an X-ray transmission process to obtain the second projection data of the subject.

In some embodiments, the plurality of scanning parameters may comprises at least one of a tube voltage of the scanner or a tube current of the scanner.

In some embodiments, the correction coefficient may be configured to correct errors induced by a detector that collects the projection data.

In some embodiments, the sample data may comprise first projection data being generated by scanning air under the scanning parameter, and the at least one processor is further configured to: determine the correction coefficient based on the first projection data and the first neural network model.

In some embodiments, the at least one processor is further configured to perform a noise reduction operation on the projection data based on the parameter, the parameter being a noise reduction parameter.

According to an aspect of the present disclosure, a non-transitory computer readable medium including executable instructions that, when executed by at least one processor, cause the at least one processor to effectuate a method, the method may comprise: obtaining sample data, the sample data comprising at least one of projection data or a scanning parameter; obtaining a first neural network model; determining the parameter based on the sample data and the first neural network model, the parameter comprising at least one of a correction coefficient or a noise reduction parameter.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 3:
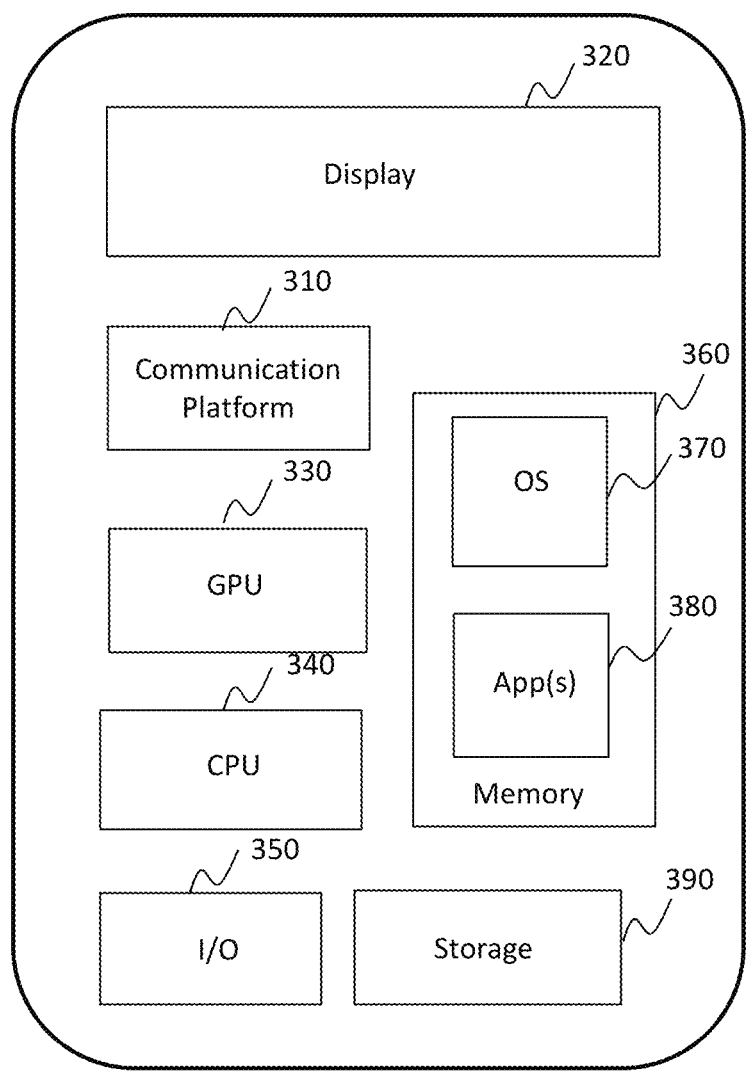
FIG. 3 is a schematic diagram illustrating exemplary hardware and/or software components of an exemplary mobile device on which the terminal may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Figure 1:
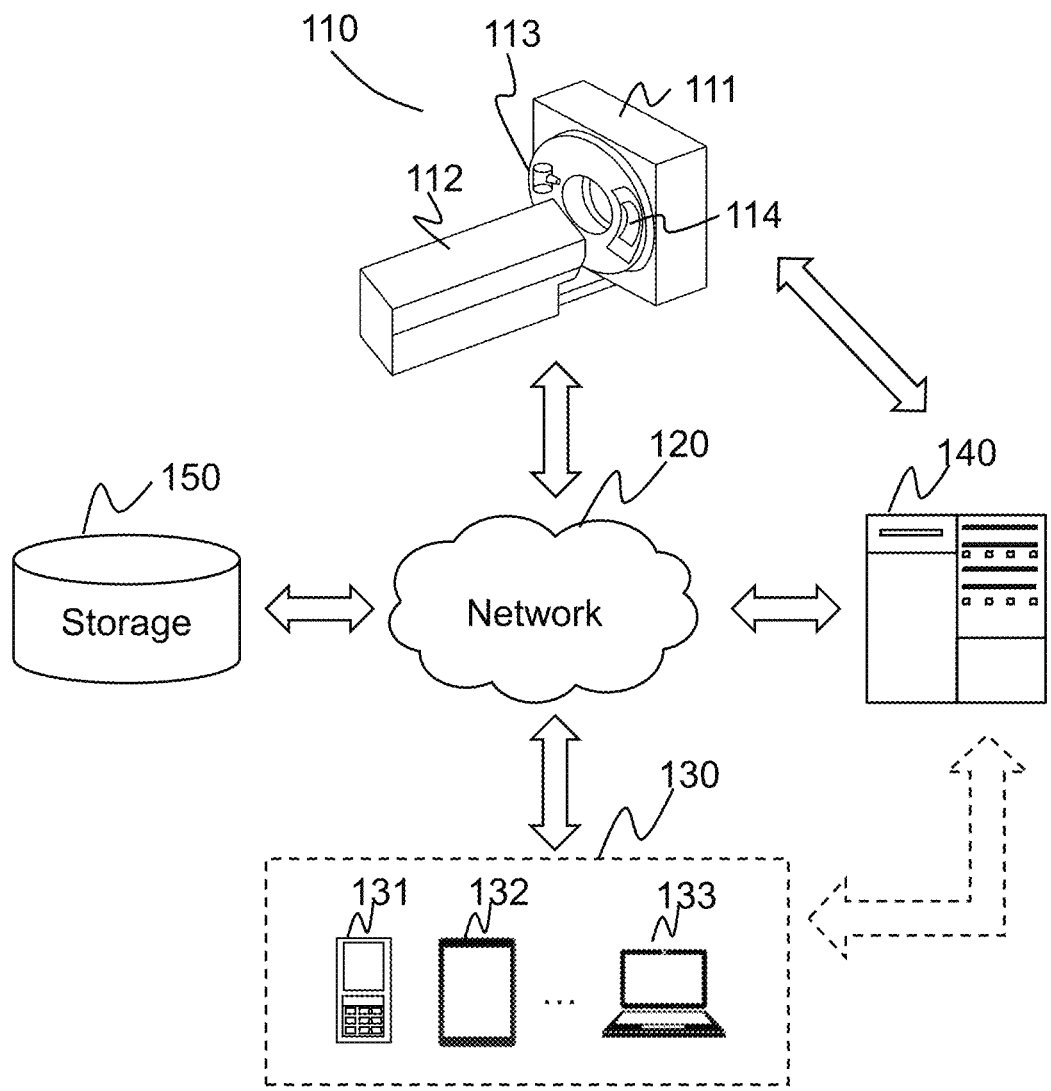
FIG. 1 is a schematic diagram illustrating an exemplary medical imaging system according to some embodiments of the present disclosure.

FIG. 1 is a schematic diagram illustrating an exemplary medical imaging system 100 according to some embodiments of the present disclosure. As shown, the medical imaging system 100 may include a scanner 110, a network 120, one or more terminals 130, a processing engine 140, and a storage device 150.

The scanner 110 may include a gantry 111, a table 112, a radiation scanning source 113 and a detector 114. The gantry 111 may support the detector 114 and the radiation scanning source 113. A subject may be placed on the table 112 for scanning. The radiation scanning source 113 may emit radiation rays (X-rays) to the subject. The detector 114 may detect radiation events (e.g., photons) emitted from radiation scanning source 113 to generate projection data. In some embodiments, the projection data may be associated with one or more scanning parameters. As used herein, a scanning parameter may be configured for the scanning process of a subject (e.g., a patient, a phantom, etc.). The scanning parameter may relate to at least one of the detector or the subject. For example, the scanning parameter may include size of the subject, scanning protocol, eccentric setting of the subject, tube voltage of the scanner, or tube current of the scanner. In some embodiments, the detector 114 may include one or more detector units. The detector units may include a scintillation detector (e.g., a cesium iodide detector), a gas detector, etc. The detector unit may be and/or include a single-row detector and/or a multi-rows detector.

The network 120 may include any suitable network that can facilitate exchange of information and/or data for the medical imaging system 100. In some embodiments, one or more components of the medical imaging system 100 (e.g., the scanner 110, the terminal 130, the processing engine 140, the storage device 150, etc.) may communicate information and/or data with one or more other components of the medical imaging system 100 via the network 120. For example, the processing engine 140 may obtain image data from the scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the CT system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may generate a neural network model and/or process medical data (e.g., projection data). The projection data may be obtained from the scanner 110, the terminal 130, and/or the storage device 150. In some embodiments, the processing engine 140 may process the projection data with a neural network to determine a processing parameter (e.g., a correction coefficient or a noise reduction parameter). As used herein, a processing parameter (or referred to as a parameter) may refer to a parameter that may be used to process medical data (e.g., the sample data illustrated elsewhere in the present disclosure). Exemplary processing parameter may include a correction coefficient, a noise reduction parameter, or the like, or any combination thereof. Detailed description may be found elsewhere in the present disclosure. In some embodiments, the processing engine 140 may be a single server or a server group. The server group may be centralized or distributed. In some embodiments, the processing engine 140 may be local or remote from other components in the system 100. The processing engine 140 may access medical data stored in the scanner 110, the terminal 130, and/or the storage device 150 via the network 120. Alternatively, the processing engine 140 may be directly connected to the scanner 110, the terminal 130 and/or the storage device 150 to access stored medical data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2.

The storage device 150 may store data, instructions, and/or any other information. In some embodiments, the storage device 150 may store data obtained from the scanner 110, the terminal 130 and/or the processing engine 140. In some embodiments, the storage device 150 may store data and/or instructions that the processing engine 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the medical imaging system 100 (e.g., the processing engine 140, the terminal 130, etc.). One or more components in the medical imaging system 100 may access the data or instructions stored in the storage device 150 via the network 120. In some embodiments, the storage device 150 may be directly connected to or communicate with one or more other components in the medical imaging system 100 (e.g., the processing engine 140, the terminal 130, etc.). In some embodiments, the storage device 150 may be part of the processing engine 140.

Figure 2:
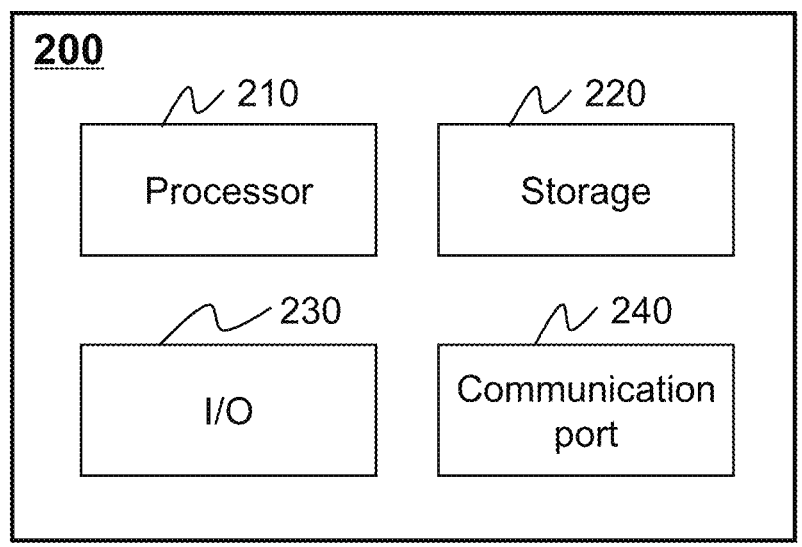
FIG. 2 is a schematic diagram illustrating an exemplary computing device on which the medical imaging system can be implemented, according to some embodiments of the present disclosure.

FIG. 2 is a schematic diagram illustrating exemplary hardware and/or software components of an exemplary computing device on which the processing engine 140 may be implemented according to some embodiments of the present disclosure. As illustrated in FIG. 2, the computing device 200 may include a processor 210, a storage 220, an input/output (I/O) 230, and a communication port 340.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process medical data obtained from the scanner 110, the terminal 130, the storage device 150, and/or any other component of the medical system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor 210 of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the scanner 110, the terminal 130, the storage device 150, and/or any other component of the medical imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing engine 130 for determining a regularization item.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication port 440 may be connected to a network (e.g., the network 140) to facilitate data communications. The communication port 240 may establish connections between the processing engine 140 and the scanner 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G, etc.), or the like, or any combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Those skilled in the art will recognize that the present teachings are amenable to a variety of modifications and/or enhancements. For example, although the implementation of various components described herein may be embodied in a hardware device, it may also be implemented as a software only solution, for example, an installation on an existing server. In addition, the processing engine 130 as disclosed herein may be implemented as a firmware, firmware/software combination, firmware/hardware combination, or a hardware/firmware/software combination.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 140. User interactions with the information stream may be achieved via the I/O 350 and provided to the processing engine 140 and/or other components of the medical imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
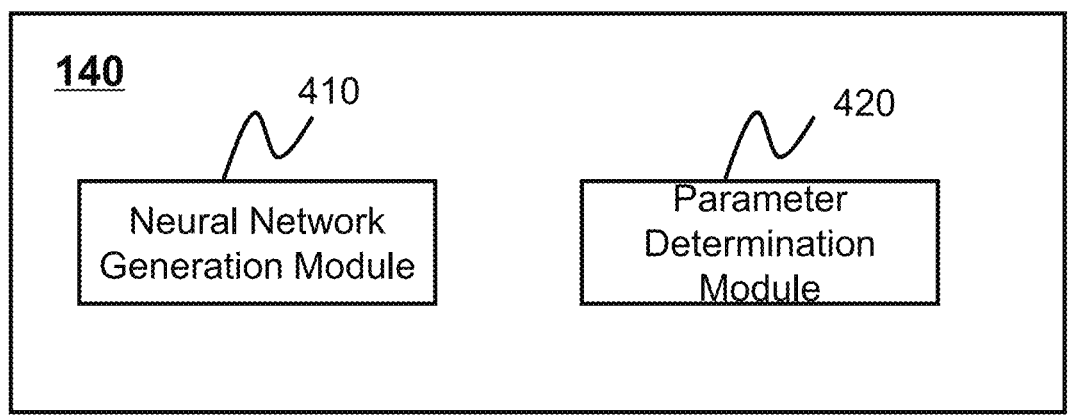
FIG. 4 is a block diagram illustrating an exemplary processing engine according to some embodiments of the present disclosure.

FIG. 4 is a block diagram illustrating an exemplary processing engine 140 according to some embodiments of the present disclosure. The processing engine 140 may include a neural network generation module 410 and a parameter determination module 420. The processing engine 140 may be implemented on various components (e.g., the processor 210 of the computing device 200 as illustrated in FIG. 2) of the medical imaging system 100. More or less components may be included in the processing engine 140 without loss of generality. For example, two of the modules may be combined into a single module, or one of the modules may be divided into two or more modules. In one implementation, one or more of the modules may reside on a same computing device or different computing devices (e.g., different server computers).

The neural network generation module 410 may be configured to generate a trained neural network model (or referred to as a first neural network model). A trained neural network may refer to a neural network model generated through a training process. Detailed description of the training process may be illustrated in FIG. 6 and the description thereof.

The neural network generation module 410 may generate the first neural network model based on an initial neural network model and training data. The initial neural network model may be generated using one or more neural network models. The parameters associated with the initial neural network model may be randomly generated. The training data may include a scanning parameter, projection data, a parameter, etc. Exemplary scanning parameters may include at least one of a tube voltage of the scanner or a tube current of the scanner. The projection data may include forward projection data of the subject. Exemplary processing parameters may include a correction coefficient, a noise reduction parameter, or the like. In some embodiments, the neural network generation module 410 may generate the first neural network model directly based on the initial neural network model and the training data. For example, the neural network generation module 410 may train the initial neural network using the training data to obtain the first neural network model. The training data may be obtained from the storage device 150 and/or the detector 114 via the network 120. In some embodiments, the training data may be pre-processed for training the initial network model. For example, the neural network generation module 410 may process first projection data of a subject (e.g., or referred to as raw projection data of a subject) to generate second projection data of the subject (or referred to as reference projection data of the subject), and generate the first neural network model using the second projection data and the initial neural network model. In some embodiments, the generated first neural network model may be used in parameter determination process performed by the parameter determination module 420.

The parameter determination module 420 may be configured to determine a parameter related to sample data, based on which the sample data may further be corrected. As used herein, the sample data may include projection data to be corrected. Exemplary sample data may include first projection data, third projection data, target projection data, which may be illustrated elsewhere in the present disclosure. In some embodiments, the parameter determination module 420 may determine the parameter based on the sample data and the first neural network model, for example, by inputting the sample data into the first neural network model.

It should be noted that the above description of the processing engine 140 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the neural network generation module 410 or the parameter determination module 420 may be implemented on processing unit, hardware or software other than the processing engine 140 yet cooperate with the processing unit 140 to perform the functions described above.

Figure 5:
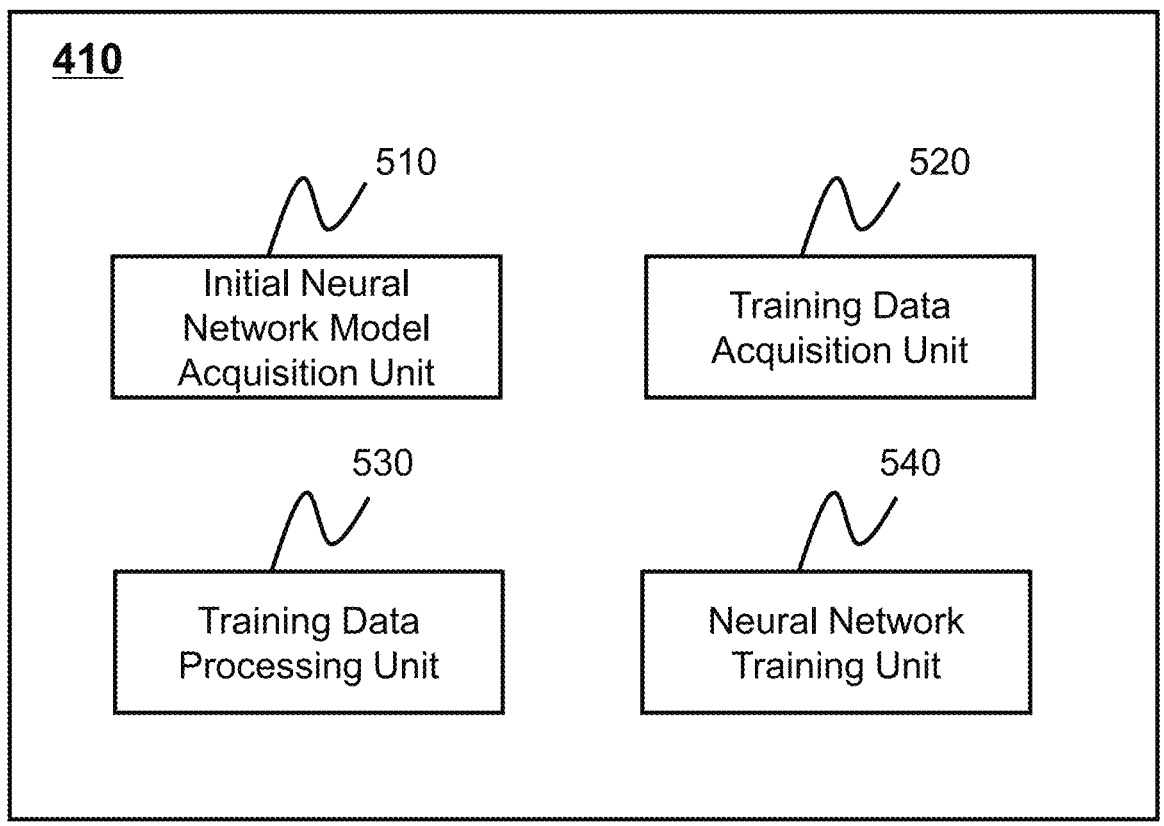
FIG. 5 is a block diagram illustrating an exemplary neural network generation module according to some embodiments of the present disclosure.

FIG. 5 is a block diagram illustrating an exemplary neural network generation module 410 according to some embodiments of the present disclosure. The neural network generation module 410 may include an initial neural network model acquisition unit 510, a training data acquisition unit 520, a training data processing unit 530 and a neural network training unit 540. More or less components may be included in the processing engine without loss of generality. For example, two of the units may be combined into a single unit, or one of the units may be divided into two or more units. In one implementation, one or more of the unit may reside on a same computing device or different computing devices (e.g., different server computers).

The initial neural network model acquisition unit 510 may be configured to obtain an initial neural network. The initial neural network model may be generated using one or more neural network models. The parameters associated with the initial neural network model may be randomly generated. In some embodiments, the initial neural network model acquisition unit 510 may obtain the neural network model by accessing the storage device 150 via the network 120. In the alternative, the initial neural network model acquisition unit 510 may construct the initial neural network model based on one or more existing neural network models. In some embodiments, the initial neural network model acquisition unit 510 may transmit the obtained initial neural network model to the neural network training unit 540.

The training data acquisition unit 520 may be configured to obtain training data. The training data may include a scanning parameter, projection data, a processing parameter, etc. In some embodiments, the training data acquisition unit 520 may obtain the training data by assessing the data stored in the storage device 150, or by assessing the detector 114, via the network 120.

In some embodiments, the training data acquisition unit 520 may transmit the training data to the training data processing unit 530 and/or the neural network training unit 540.

The training data processing unit 530 may be configured to process the training data. The training data processing unit 530 may process the training data by various operations, such as analyzing, classifying, filtering, correcting, etc. In some embodiments, the training data processing unit 530 may process first projection data of a subject (e.g., or referred to as raw projection data of a subject) to generate second projection data of the subject (or referred to as reference projection data of the subject). In some embodiments, the training data processing unit 530 may transmit the processed training data to the neural network training unit 540.

The neural network training unit 540 may be configured to train the initial neural network model to obtain a trained neural network model. The neural network training unit 540 may train the neural network model with training data received from the training data acquisition unit 520 or with the processed training data received from the training data processing unit 530. The training process of the neural network model may be illustrated elsewhere in the present disclosure. In some embodiments, the neural network training unit 540 may send the trained neural network model to the parameter determination module 420 for subsequent operations, or may store the trained neural network model in the storage 220 of the processing engine 140 or the storage device 150.

It should be noted that the above description of the neural network generation module 410 is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure. For example, the function of the training data processing unit 530 may be implemented in the training data acquisition unit 520, and thus, the training data processing unit 530 and the training data acquisition unit 520 may be combined as one unit.

Figure 6:
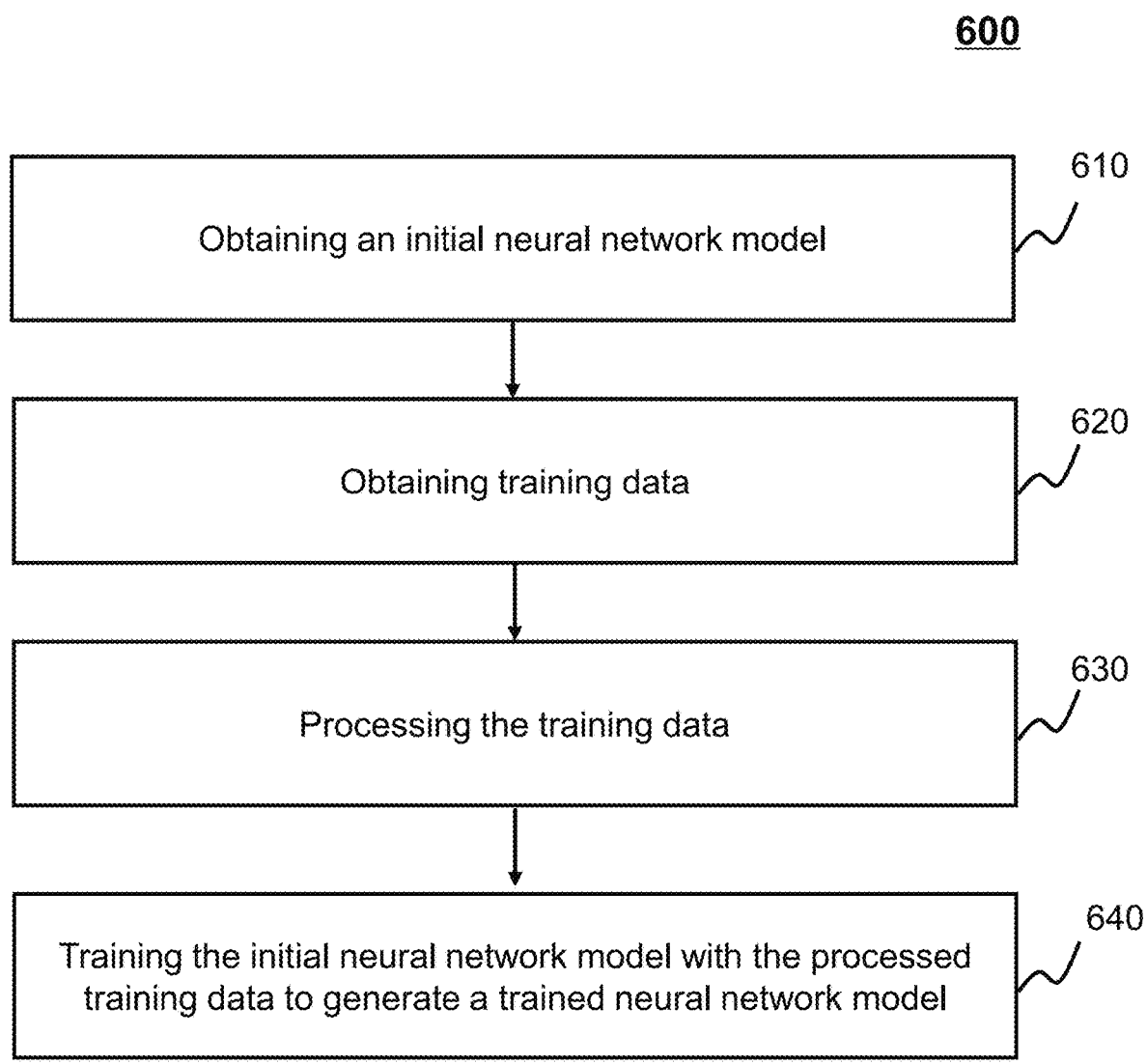
FIG. 6 is a flowchart illustrating an exemplary process for training an initial neural network model according to some embodiments of the present disclosure.

FIG. 6 is a flowchart illustrating an exemplary process 600 for training an initial neural network model according to some embodiments of the present disclosure. Process 600 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 600 may be performed by or be implemented on the processing engine 140 of the medical imaging system 100.

In 610, the initial neural network model acquisition unit 510 may obtain an initial neural network model. The initial neural network model acquisition unit 510 may obtain the neural network model by accessing the storage device 150 via the network 120, or may construct the neural network model directly according to specific application scenario.

In some embodiments, the initial neural network model may be generated using one or more neural network models. The parameters associated with the initial neural network model may be randomly generated In some embodiments, the neural network may include a BP neural network, a recurrent neural network feedback neural network, a radial basis function neural network, a self-organizing neural network, a convolutional neural network, a perceptron neural network, a linear neural network, or the like.

In 620, the training data acquisition unit 520 may obtain training data. In some embodiments, the training data may be obtained by assessing the data stored in the storage device 150 via network 120, or by assessing the detector 114 via the network 120.

The training data may include a scanning parameter, projection data (e.g., raw projection data of a phantom, air projection data, projection data with noise, etc.), a parameter (reference correction coefficient), etc. As used herein, raw projection data may refer to projection data that are collected by detectors and generated by scanning a phantom. Air projection data may refer to projection data generated by scanning air. Projection data with noise may refer to projection data with known noise distribution. Reference correction coefficient may be generated through conventional correction method or physical simulation. For example, the reference correction coefficient may be generated by smoothing the raw projection data. As another example, the reference correction coefficient may be generated by simulating transmission paths of X-ray photons.

In 630, the training data processing unit 530 may process the training data. In some embodiments, the training data obtained in operation 620 may be further processed for training the initial neural network. In some embodiments, the training data may be processed to obtain processed training data by analyzing, classifying, filtering, or other operations. Merely by way of example, the raw projection data of the phantom may be processed to generate reference projection data, which may further be used to train the initial neural network.

In 640, the neural network training unit 540 may train the initial neural network model with the training data and/or the processed training data to generate a trained neural network model.

In some embodiments, the training data and/or the processed training data may be input into the initial neural network model to train the model. The training process for the neural network model may include a plurality of training iterations. The one or more parameters of the neural network model may be updated during each training iteration. The updated one or more parameters of the neural network model may be used as input for the next training iteration. When the neural network model satisfies a condition, for example, the difference between the actual output value and the desired output is less than a threshold, or a certain number of training iterations have been performed, the training process may terminate. The one or more parameters generated in the last training iteration may be saved with the trained neural network. In some embodiments, the trained neural model may be used to determine some parameters related to projection data, for example, correction coefficient, noise reduction parameter, or the like.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. Merely by way of example, an operation for storing the obtained training data may be added between operation 620 and operation 630.

Figure 7:
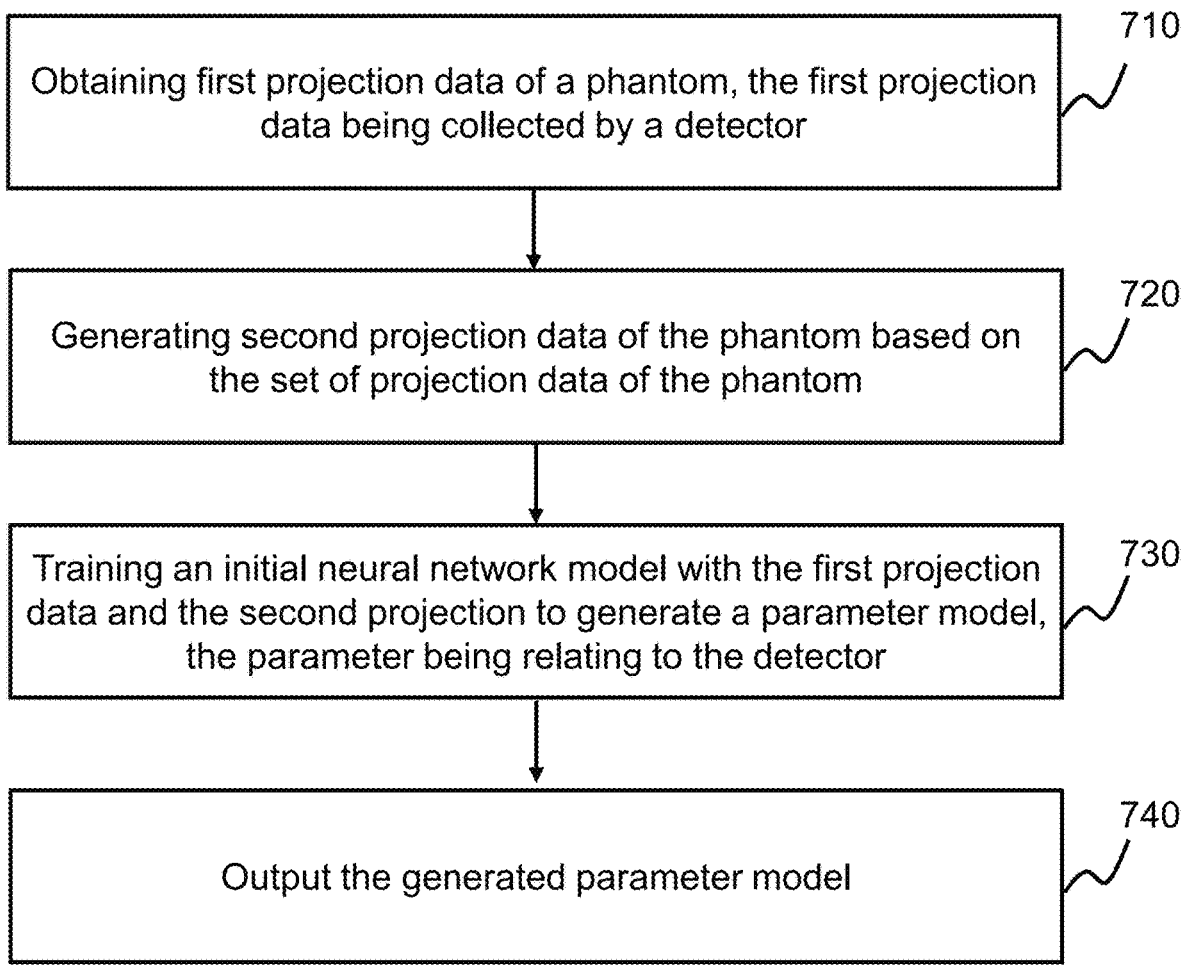
FIG. 7 is a flowchart illustrating an exemplary process for training a parameter model according to some embodiments of the present disclosure.

FIG. 7 is a flowchart illustrating an exemplary process 700 for training a parameter model according to some embodiments of the present disclosure. Process 700 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 700 may be performed by or be implemented on the processing engine 140 of the medical imaging system 100.

In 710, the training data acquisition unit 520 may obtain first projection data of a phantom (or referred to as first projection data of a subject).

In some embodiments, the phantom may be a specially designed subject that is scanned or imaged in the field of medical imaging to evaluate, analyze, and tune the performance of various imaging devices. For example, the phantom may be designed as a shape of a living subject such as a human body or an animal. In some embodiments, the first projection data may be raw projection data of the phantom collected by a detector. The detector may detect the traversed radiation beams and generate the raw projection data of the phantom. In some embodiments, the first projection data may correspond to a plurality of scanning parameters. The plurality of scanning parameters may be related to at least one of the detector or the phantom. In some embodiments, the plurality of scanning parameters may include at least one of a tube voltage of the scanner or a tube current of the scanner. For example, a phantom may be scanned at difference tube voltages and currents of the scanner, and/or different detection angles to obtain the first projection data.

In 720, the training data processing unit 530 may generate second projection data of the phantom (or referred to as second projection data of the subject) based on the first projection data of the phantom.

In some embodiments, the second projection data may be reference projection data of the phantom. The training data processing unit 530 may perform data processing operations (e.g., correction, simulation, calculation, etc.) based on the first projection data of the phantom to obtain the reference projection data of the phantom. In some embodiments, the reference projection data may be obtained by correcting the first projection data through a conventional correction method and/or physical simulation. For example, as the structure and the form of the phantoms are fixed and known, the reference projection data may be obtained by correcting artifacts of the raw projection data by calculation or simulation.

In some embodiments, the second projection data of the phantom may be obtained by a variety of methods. For example, an image of the phantom reconstructed from the raw data may be smoothed. Then, an orthogonal projection operation may be performed on the smoothed reconstruction image to obtain the second projection data. As another example, due to the fact that the phantom are generally simple in structure, the second projection data may be obtained by calculating analytic equations of an X-ray transmission process after modelling the phantom. The phantom may be modeled according to the first image. As still another example, the second projection data may be obtained by simulating transmission paths of X-ray photons (such as Monte Carlo simulation) after digitizing the structure of the phantom. As still another example, the second projection data may be obtained by smoothing the raw projection data directly. It should be noted that the methods described above for obtaining the second projection data of the phantom are merely provided for the purposes of illustration, and not intended to limit the scope of the present disclosure.

In 730, the neural network training unit 540 may train an initial neural network model with the first projection data and the second projection data to generate a parameter model.

In some embodiments, the initial neural network model may be a parameter initialization neural network model. The initial neural network model may be generated using one or more neural network models. The parameters associated with the initial neural network model may be randomly generated. In some embodiments, the neural network may include a BP neural network, a recurrent neural network, a feedback neural network, a radial basis function neural network, a self-organizing neural network, a convolutional neural network, a perceptron neural network, a linear neural network, or the like. The parameter may be related to the detector. For example, the parameter may include a correction coefficient. The generated parameter initialization neural network model may be used to obtain a correction coefficient of projection data. In some embodiments, the correction coefficient may be configured to correct an artifact related to the projection data. In some embodiments, the correction coefficient may be configured to correct errors induced by the detector which is used to collect the projection data. In some embodiments, the parameters of the parameter initialization neural network model may be a parameter that is randomly initialized. The neural network training unit 540 may train the parameter initialization neural network model with training samples (e.g., the first projection data and the second projection data). Then, the neural network training unit 540 may perform a reverse adjustment operation on the parameters of the parameter initialization neural network model. In some embodiments, the reverse adjustment operation may be an iterative operation. After the model is trained with the training samples, the parameters of the model may be changed and the changed parameters may be designated as an "initialization parameter" for the next training process. In some embodiments, the reverse adjustment operation may be performed by using an optimization function. In some embodiments, the optimization function may be represented according to equation (1):

$$\min \| \{coef_i\} - \{coef_i\}_{ideal} \| \qquad (1)$$

wherein $\{coef_i\}$ denotes the output value of the initial neural network model, $\{coef_i\}_{ideal}$ denotes the reference output value of the training sample. Equation (1) may be used to adjust the parameters of the model to minimize the difference between the output value of the model $\{coef_i\}$ and the reference output value of the training sample $\{coef_i\}_{ideal}$. After trained with a plurality of training samples, the parameters of the initial neural network model may be determined. The training process may be ended and the neural network training unit 540 may generate a parameter model. In some embodiments, the parameter model may be a neural model obtained after the initial neural network model has been optimized. The parameter model may meet a condition, for example, the difference between the actual output and the desired output of the parameter model under the parameters is less than a threshold, and the parameters may be fixed.

In 740, the neural network training unit 540 may output the parameter model. In some embodiments, the neural network training unit 540 may store the parameter model in the storage 220 of the processing engine 140 or in the storage device 150, or may send the parameter model to user of the terminal 130 via the network 120.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 740 may be unnecessary and may be omitted. The neural network training unit 540 may directly process new projection data by using the parameter model.

Figure 8:
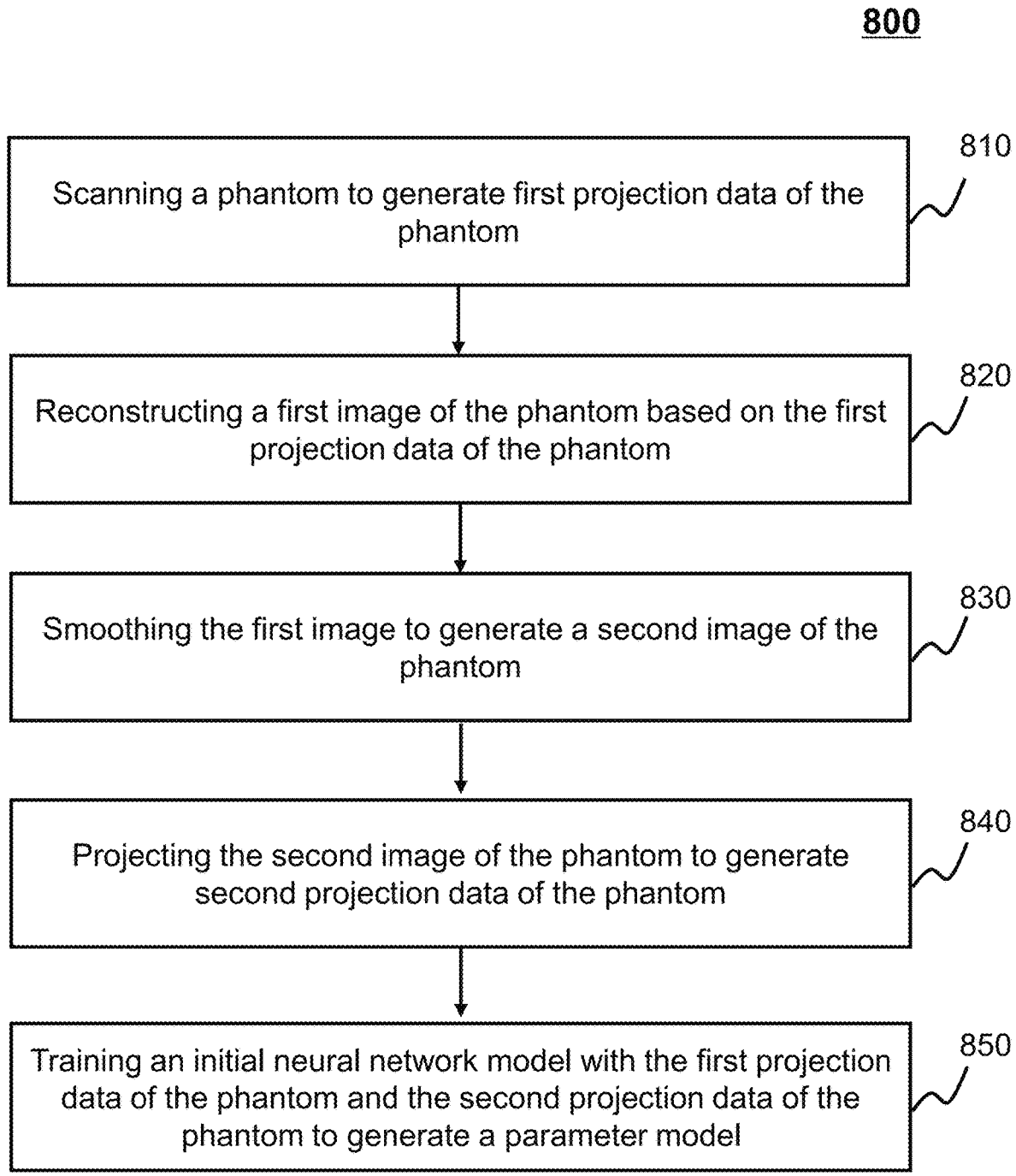
FIG. 8 is a flowchart illustrating an exemplary process for training a parameter model according to some embodiments of the present disclosure.

FIG. 8 is a flowchart illustrating an exemplary process 800 for training a parameter model according to some embodiments of the present disclosure. Process 800 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 800 may be performed by or be implemented on the processing engine 140 of the medical imaging system 100.

In 810, the training data acquisition unit 520 may obtain first projection data of a phantom by scanning the phantom. In some embodiments, the phantom may be a specially designed object that is scanned or imaged in the field of medical imaging to evaluate, analyze, and tune the performance of various imaging devices. For example, the phantom may be designed as a shape of a living subject such as a human body or an animal. In some embodiments, the first projection data may be raw projection data of the phantom. In some embodiments, one or more sizes of the phantom may be scanned and the raw data of the plurality of phantoms may be obtained. In some embodiments, a phantom with a certain size may be scanned under different eccentric settings and the raw data of the phantom may be obtained.

In 820, the training data processing unit 530 may reconstruct a first image of the phantom based on the first projection data of the phantom. In some embodiments, the first image may be a raw image of the phantom. The raw image may be obtained by an image reconstruction method based on the raw projection data (e.g., the first projection data). In some embodiments, the image reconstruction method may include a filter back projection algorithm, an algebraic reconstruction algorithm, a local reconstruction algorithm, or the like.

In 830, the training data processing unit 530 may smooth the first image to reduce a ring artifact of the phantom and generate a second image of the phantom. For example, the smoothing operation may be implemented on a normalized box filter, a Gaussian filter, a median filter, or the like.

In 840, the training data processing unit 530 may project (e.g., forward project) the second image of the phantom to generate second projection data of the phantom. In some embodiments, the second projection data may be reference projection data of the phantom. The projecting operation may include an orthographic projection, a parallel projection, a central projection, or the like, or any combination thereof.

In 850, the neural network training unit 540 may train an initial neural network model with the first projection data and the second projection data to generate a parameter model. In some embodiments, the operation 850 may be similar to the operation 730 and the description may be found in elsewhere of the present disclosure (e.g., FIG. 7).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, a step in which the first image or second image may be stored may be added to the process 800.

Figure 9:
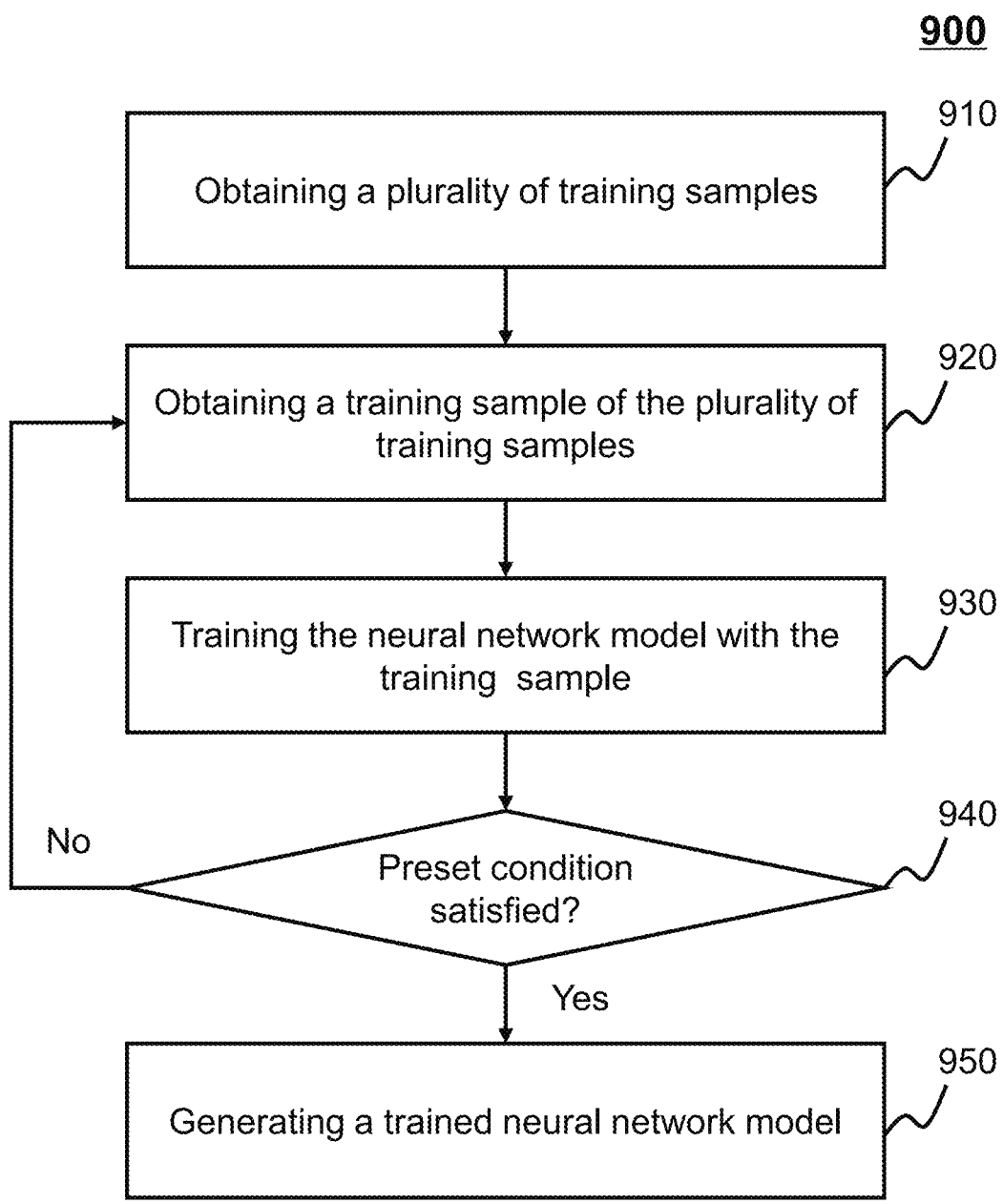
FIG. 9 is a flowchart illustrating an exemplary process for training a parameter model according to some embodiments of the present disclosure.

FIG. 9 is a flowchart illustrating an exemplary process 900 for training a parameter model according to some embodiments of the present disclosure. Process 900 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 900 may be performed by or be implemented on the processing engine 140 of the medical imaging system 100.

In 910, the training data acquisition unit 520 may obtain a plurality of training samples.

In some embodiments, the training sample may include an input value and/or a reference output value. The input value may be input into the neural network to obtain output value. The reference output value may be used during calculating a difference between the output value and the reference output value. In some embodiments, the input value may include at least one of a second scanning parameter or second projection data. The second scanning parameter may include a voltage of the X-ray tube, an electric current of the X-ray tube, scanning time, slice thickness, pitch, scanning volume, or the like. The second projection data may include projection data generated by scanning air under the second scanning parameter. In some embodiments, the reference output value may include one or more reference correction coefficients. The reference correction coefficient may be an ideal correction coefficient. The ideal correction coefficient may be obtained by calculating projection data of standard phantom after scanning. The standard phantom may refer to a subject with known production material and/or structural parameters. For example, the standard phantom may be a cylinder of 20 centimeters in diameter and 10 centimeters in height made by transparent plastic. The method of obtaining the reference correction coefficient by scanning the standard phantom may be known for a person having ordinary skill in the art, and the description may not be repeated in the present disclosure.

In some embodiments, the training sample may include a second scanning parameters, a second projection data and a reference correction coefficient corresponding to the second scanning parameters. In some embodiments, the training sample may include a second projection data and a reference correction coefficient corresponding to the second scanning parameters. In some embodiments, the training sample may include a second scanning parameter and a reference correction coefficient corresponding to the second scanning parameters. In some embodiments, the plurality of training samples may be stored in the storage device 150 or the storage 220 of the processing engine 140. The training data acquisition unit 520 may obtain the training samples by accessing the storage device 150 and/or the storage 220 of the processing engine 140 via the network 120.

In 920, the training data acquisition unit 520 may obtain a training sample of the plurality of training samples. The training sample may include a reference correction coefficient.

In 930, the neural network training unit 540 may train the neural network model with the training sample.

In some embodiments, the neural network training unit 540 may obtain the neural network model by accessing the storage device 150 via the network 120, or may construct the neural network model directly. The parameters associated with the initial neural network model may be randomly generated. In some embodiments, the neural network training unit 540 may input the training sample into the neural network model and obtain an output after a pre-determined calculation processing (e.g., feature extraction, feature identification, or the like, or any combination thereof) performed by the neural network model. Then, the neural network training unit 540 may perform a reverse adjustment operation on the parameters of the neural network model by using an optimization function. In some embodiments, the reverse adjustment operation may be performed according to equation (2):

$$\min \|\{a_i\} - \{a_i\}_{ideal}\| \qquad (2)$$

wherein $\{a_i\}$ denotes the output value of the initial neural network model, $\{a_i\}_{ideal}$ denotes the reference output value of the training sample. Equation (2) may be used to adjust the parameters of the model to obtain a minimum difference between output value of the model and the reference output value of the training sample. The parameters of the model may be updated in each training iteration and the updated parameters may be designated as an "initialization parameter" for the next training iteration.

In 940, the neural network training unit 540 may determine whether the neural network model is satisfied with a preset condition.

In some embodiments, the preset condition may be determined by the user. For example, the preset condition may be that the number of the trained training samples reaches a preset value determined by the user. In some embodiments, the preset condition may be that the neural network model has been verified and the verification result is qualified. The verification may be conduct based on a difference between the output of the neural network model and the reference correction coefficient. For example, a new sample may be input into the neural network model and a correction coefficient corresponding to the new sample may be obtained. Comparing the correction coefficient with the reference correction coefficient, if the difference between the correction coefficient and the reference correction coefficient is smaller than a pre-set value (e.g., the pre-set value may be default settings of the processing engine 140, or may be adjusted by a user (e.g., a doctor) under different situations), the verification of the neural network model may be qualified. Otherwise, the neural network model may continue to be trained. In some embodiments, if the preset condition is satisfied, the process 900 may proceed to 950. In 950, the neural network training unit 540 may generate a trained neural network model. The trained neural network model may be stored in the storage 220 of the processing engine 140 and/or the storage device 150, or may be sent to user of the terminal 130 via the network 120. If the preset condition is not satisfied, the process 900 may proceed to 920. The neural network training unit 540 may continue to train the neural network model with new training samples until the preset condition is satisfied.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 910 may be omitted, a training sample may be obtained in operation 920.

Figure 10:
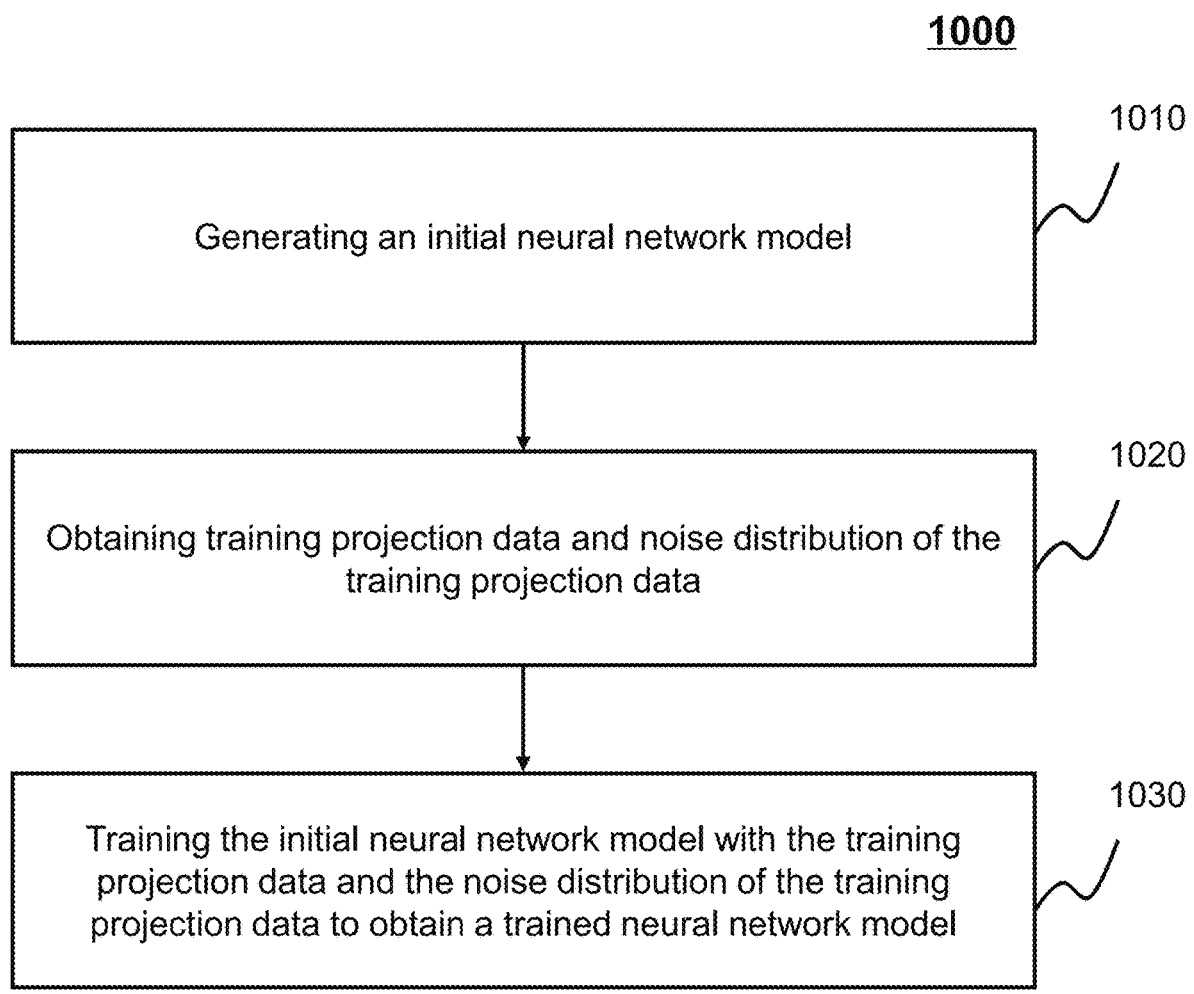
FIG. 10 is a flowchart illustrating an exemplary process for training a parameter model according to some embodiments of the present disclosure.

FIG. 10 is a flowchart illustrating an exemplary process 1000 for training a parameter model according to some embodiments of the present disclosure. Process 1000 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 1000 may be performed by or be implemented on the processing engine 140 of the medical imaging system 100.

In 1010, the initial neural network acquisition unit 510 may generate an initial neural network model. In some embodiments, the initial neural network model may be generated using one or more neural network models. The parameters associated with the initial neural network model may be randomly generated.

In 1020, the training data acquisition unit 520 may obtain training projection data and noise distribution of the training projection data.

In some embodiments, the training projection data may include projection data with noise and a noise reduction parameter. The noise may refer to the impact of various interferences on the data during the data acquisition process and/or data transmission process. For example, in a medical imaging system, the decrease of the electric current of the X-ray tube under the same conditions may lead to a decrease in the signal-to-noise ratio of the projection data. The noise distribution may refer to the distribution of noise in the projection data. In some embodiments, the noise may demonstrate a temporal distribution. For example, electromagnetic interference at different time points may be a noise signal added into the projection data. In some embodiments, the noise may demonstrate a spatial distribution. For example, for a certain X-ray incidence angle, because the detection angles of the detector in different channels are different, the collected projection data may have a certain spatial distribution. The noise added to the projection data may also have a spatial distribution. In some embodiments, the noise may include Gaussian noise, white noise, salt and pepper noise, shot noise, quantization noise, anisotropic noise, periodic noise, or the like, or any combination thereof. The noise reduction parameter may include spectrum parameter of the noise distribution, threshold of the wavelet decomposition, regularization term coefficient of the total variation, or the like, or any combination thereof. In some embodiments, the projection data for training the initial neural network may be a combination of low noise projection data and simulated noise data with known noise distribution. The training data processing unit 530 may process the projection data to obtain the noise reduction parameter of the projection data.

In 1030, the neural network training unit 540 may train the initial neural network model with the projection data and the noise distribution of the projection data to obtain a trained neural network model.

In some embodiments, the neural network training unit 540 may constantly adjust the parameters associated with the neural network based on a loss function, and may obtain the trained neural network model when the loss function reaches minimum. The parameters associated with the neural network may be a parameter of neuron including weight that can be learned and bias constant. The weight may be used to measure the effect of neuron which is close to the input layer on the neuron which is far from the input layer. The bias constant may be initialized randomly to avoid the output of neurons being constant zero. In some embodiments, the loss function may be a function to measure loss and error degree between an actual output value and a desired output value. In the present disclosure, the objective of the training process may be to minimize the loss function of the neural network, e.g., to minimize the difference between the estimated output value and the desired output value. In some embodiments, the projection data may include a desired output value. The desired output value may be related to the noise reduction parameter of the projection data. For example, the desired output data may include one or more parameters related to the noise distribution of the projection data. The actual output value may be the same type of the parameter as the desired output value. For example, if the desired output value is the spectrum parameter of the noise distribution of the projection data, the actual output value may be a spectrum parameter obtained by calculating the projection data by the neural model.

In some embodiments, the loss function may be expressed according to equation (3):

$$f(x) = \min\|\{X_i\} - \{X_i\}_0\| \quad (3)$$

Wherein $\{X_i\}$ denotes a value set of the actual output value of the neural network model, $\{X_i\}_0$ denotes a value set of the desired output value of the projection data neural network model. In some embodiments, $\{X_i\}$ and $\{X_i\}_0$ may be represented by vectors, for example, $\{X_i\}$ may be represented by $[x_{11}, x_{12}, \ldots x_{1n}]$, $\{X_i\}_0$ may be represented by $[x_{01}, x_{02}, \ldots x_{0n}]$, wherein $x_{11}$ denotes an actual output value of the neural network model, $x_{01}$ denotes a desired output value of the neural network model. $\min\|\{X_i\} - \{X_i\}_0\|$ may represent the minimum of L2 norm of $\{X_i\} - \{X_i\}_0$. $\|\{X_i\} - \{X_i\}_0\|$ may represent a difference between $\{X_i\}$ and $\{X_i\}_0$. In some embodiments, $\|\{X_i\} - \{X_i\}_0\|$ may be determined according to equation (4):

$$\|\{X_i\} - \{X_i\}_0\| = \sqrt{\sum_{k=1}^{n}(x_{1k} - x_{0k})^2} \quad (4)$$

In some embodiments, the neural network training unit 540 may train different types of neural network models based on the desired output value of the neural network. For example, if the desired output value is the spectrum parameter of the noise distribution, the loss function may be represented as $\min\|\{F_i\} - \{F_i\}_0\|$, wherein $\{F_i\}$ denotes the desired output value (desired noise spectrum parameter), $\{F_i\}_0$ denotes the noise spectrum parameter of the training projection data based on the current neural network model. The trained neural network model may be used to obtain the spectrum parameter of new projection data. As another example, if the desired output value is the threshold of the wavelet decomposition, the loss function may be represented as $\min\|\{Th_i\} - \{Th_i\}_0\|$, wherein $\{Th_i\}$ denotes the desired output value, $\{Th_i\}_0$ denotes the threshold of the wavelet of the training projection data based on the current neural network model. The trained neural network model may be used to obtain the threshold of the wavelet decomposition of new projection data. As still another example, if the desired output value is the regularization term coefficient of the noise distribution, the loss function may be represented as $\min\|\{Coef_i\} - \{Coef_i\}_0\|$, wherein $\{Coef_i\}$ denotes the desired output value, $\{Coef_i\}_0$ denotes the regularization term coefficient of the noise distribution of the training projection data based on the current neural network model. The trained neural network model may be used to obtain the regularization term coefficient of the noise distribution of new projection data.

In some embodiments, the neural network training unit 540 may constantly adjust the value of the model parameter until the loss function reached the minimum value during the training process. In some embodiments, the neural network training unit 540 may reduce overfitting by adding a penalty term into the loss function to accelerate the convergence of the model. The overfitting may refer to a situation that the trained neural network has good performance in training data recognition but poor performance in actual practice. The overfitting may be caused by training the model using excessive detail features, including non-common features. The penalty term may also be referred to as regular term. The regular term may include a L1 normal form regularization function, a L2 normal form regularization function, or the like, or any combination thereof.

In some embodiments, the neural network training unit 540 may obtain the trained neural network model when the loss function reaches the minimum. After the training process converges, the trained neural network model may be tested, and the parameters associated with the neural network may not be changed during the testing process. The test sample may be extracted from the sample data sets stored in the storage device 150, and may be different from the training project data. After the loss function is confirmed to reach the minimum by the test, the training for the model may be considered to be completed. The neural network training unit 540 may store the trained neural network in the storage 220 of the processing engine 140 and/or the storage device 150, or may be sent to user of the terminal 130 via the network 120.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, a step in which the training projection data and the noise distribution of the training projection data may be stored may be added to the process 1000.

Figure 11:
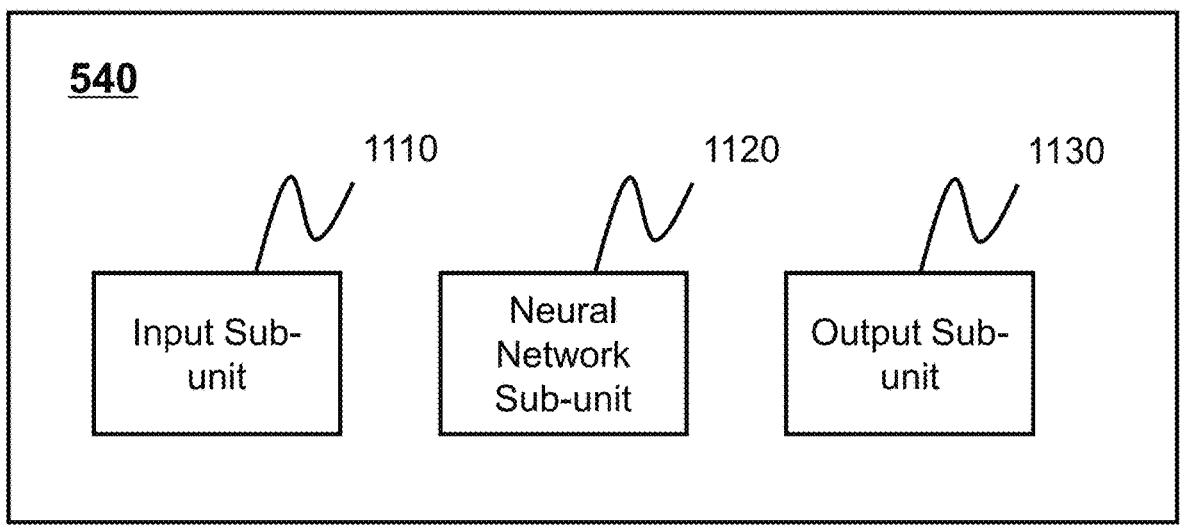
FIG. 11 is a schematic diagram illustrating an exemplary neural network training unit according to some embodiments of the present disclosure.

FIG. 11 is a block diagram illustrating an exemplary neural network training unit 540 according to some embodiments of the present disclosure. The neural network training unit 540 may include an input sub-unit 1110, a neural network sub-unit 1120 and an output sub-unit 1130. More or less components may be included in the processing engine without loss of generality. For example, two of the sub-units may be combined into a single sub-unit, or one of the sub-units may be divided into two or more sub-units. In one implementation, one or more of the sub-units may reside on a same computing device or different computing devices (e.g., different server computers).

The input sub-unit 1110 may obtain an input value and input the input value into the neural network sub-unit 1120. In some embodiments, the input value may include the raw projection data of a phantom, reference projection data of the phantom, scanning condition, air projection data, scanning parameter, reference correction coefficient corresponding to the scanning parameter, projection data with noise, noise reduction parameter, or the like, or any combination thereof.

The neural network sub-unit 1120 may perform a calculation process on the input values and obtain operation results. The calculation process may include feature extraction, feature identification, or the like, or any combination thereof. In some embodiments, the neural network sub-unit 1120 may include one or more operation layers. Each of the one or more operation layers may include one or more nodes. Each of the one or more nodes may include one or more parameters. The number of the one or more operation layers, the one or more nodes and the one or more parameters may be predetermined numbers determined by the system 100, or may be adjusted according to different application scenarios by a user. In some embodiments, each node may obtain the operation results of all nodes of the previous operation layer as the input of the node. The nodes of the first layer may obtain all the input values. The operation results of the nodes of the last operation layer may be sent to the output sub-unit 1130.

The output sub-unit 1130 may obtain the operation results of the neural network sub-unit 1120 and designate the operation results as the output value. In some embodiments, the output value may include a correction coefficient, a spectrum parameter of the noise, thresholds of each layer of the wavelet decomposition, regularization term coefficient of the total variation, or the like, or any combination thereof. In some embodiments, the output value may be related to the number of the node of the last operation layer. The more the number of nodes, the more the number of the output values.

It should be noted that the above description of the neural network generation module 410 is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure.

Figure 12:
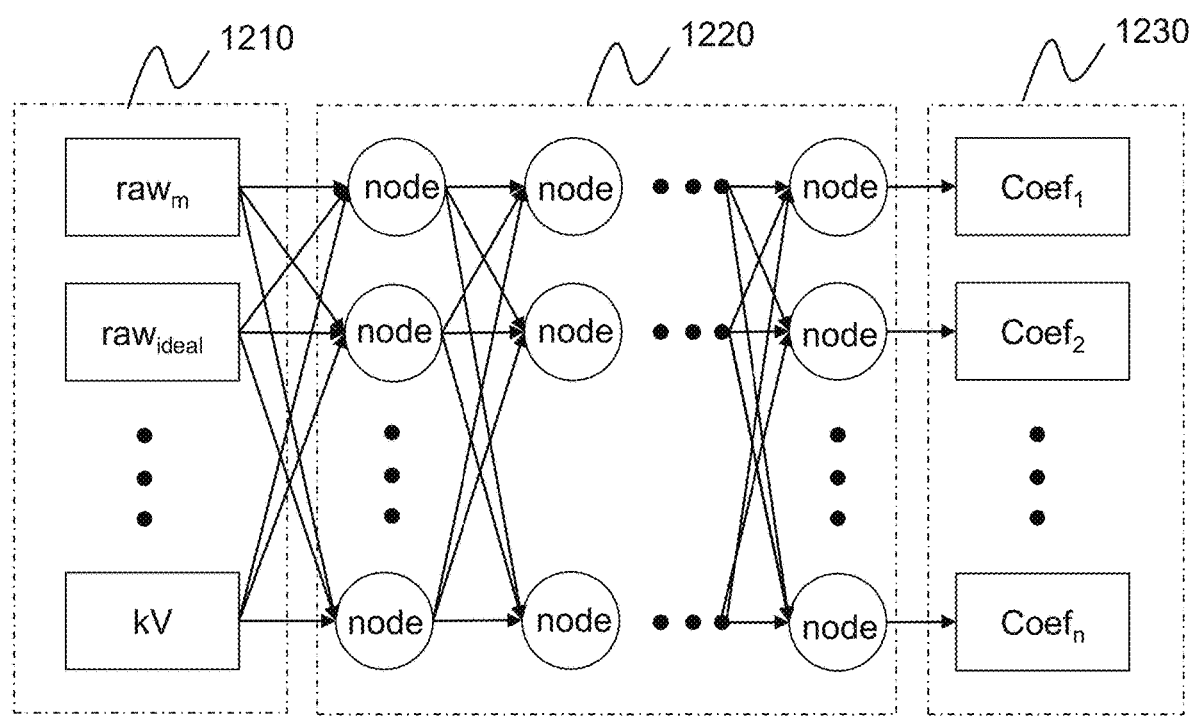
FIG. 12 is a schematic diagram illustrating an exemplary neural network model according to some embodiments of the present disclosure.

FIG. 12 is a block diagram illustrating an exemplary neural network model 1200 according to some embodiments of the present disclosure. The neural network model 1200 may be generated through the process 700 illustrated in FIG. 7 and/or FIG. 8. The neural network model 1200 may include an input terminal 1210, a neural network layer 1220 and an output terminal 1230. More or less components may be included in the neural network model without loss of generality. For example, the input terminal may be the input layer of the neural network layers, or the neural network layers may be divided into two or more independent network layers.

As shown in FIG. 12, the input terminal 1210 may obtain input values and input the input values into the neural network layer 1220. The input values of the input terminal 1210 may include the raw projection data $raw_m$, reference projection data $raw_{ideal}$, scanning condition kV, or the like. The neural network model 1200 may obtain a set of correction coefficients $\{coef_i\}$ at the output terminal 1230 by weighting multiple interconnected neuron nodes in the neural network layer 1220 with each other and converting by a function, and i denotes the number of the neural nodes of the last operation layer of the neural network layer 1220. The training set of the neural network model 1200 is the reference correction coefficients obtained under multiple protocols. In some embodiments, the reference correction coefficients may be obtained by a conventional correction method, or may be obtained by physical simulation. After being trained by data set, the neural network model 1200 may obtain a correction coefficient of new projection data based on the reference projection data and the new projection data. The correction coefficient may be used to correct the ring artifacts of the new projection data.

Figure 13:
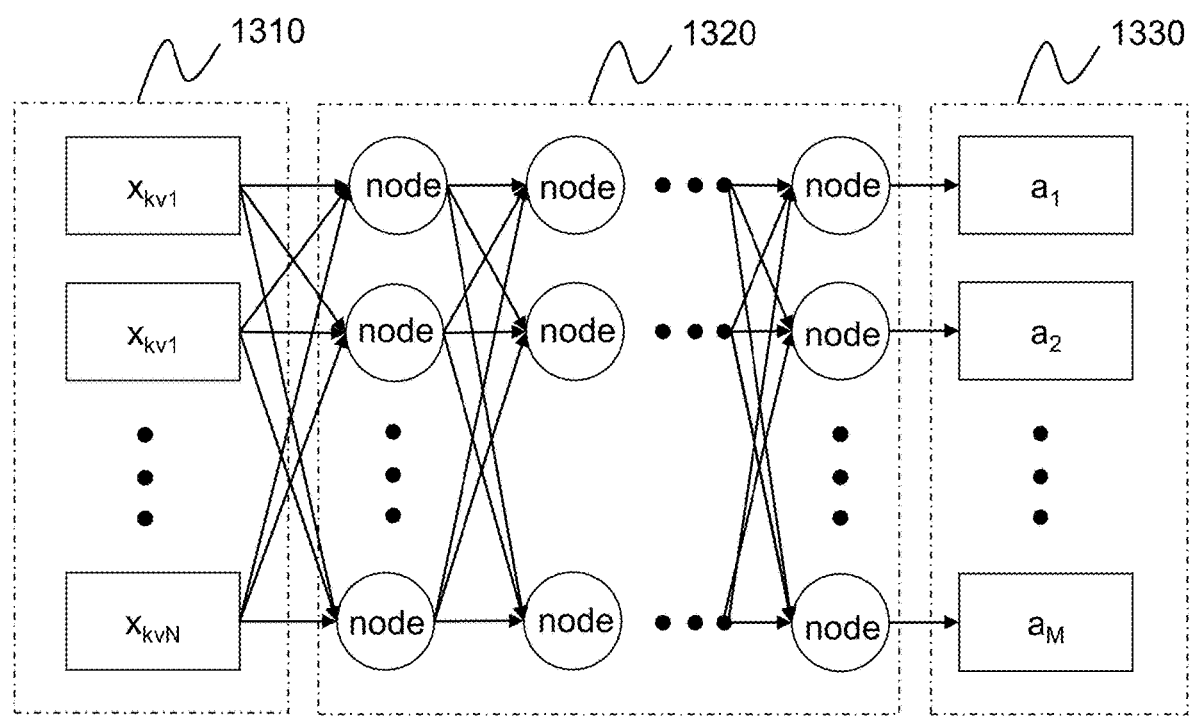
FIG. 13 is a schematic diagram illustrating an exemplary neural network model according to some embodiments of the present disclosure.

FIG. 13 is a block diagram illustrating an exemplary neural network model 1300 according to some embodiments of the present disclosure. The neural network model 1300 may be generated through the process 900 illustrated in FIG. 9. The neural network model 1300 may include an input terminal 1310, a neural network layer 1320 and an output terminal 1330. More or less components may be included in the neural network model without loss of generality. For example, the input terminal may be the input layer of the neural network layers, or the neural network layers may be divided into two or more independent network layers.

As shown in FIG. 13, the input terminal 1310 may obtain input values and input the input values into the neural network layers 1320. The input values of the input terminal 1320 may include one or more values, such as $x_{kV1}$, $x_{kV2}$, . . . , $x_{kVN}$. The one or more values may include projection data, scanning parameters, air projection data, or the like, or any combination thereof. The neural network layer 1320 may perform a calculation process on the input values and obtain operation results. The calculation process may include feature extraction, feature identification, or the like, or any combination thereof. In some embodiments, the correction coefficient generation sub-unit 1531 rather than the neural network layer 1320 may perform the calculation process. Detailed description may be found in FIG. 15 and the description thereof. The neural network layer 1320 may include one or more operation layers. Each of the one or more operation layers may include one or more node. Each of the one or more nodes may include one or more parameters. Each node may obtain the operation results of all nodes of the previous operation layer as the input of the node, and may output the operation result to all nodes of the next operation layer. The nodes of the first layer may obtain all the input values. The nodes of the last layer may send the operation results to the output terminal 1330. The output terminal 1330 may obtain the operation results of the neural network layer 1320 and designate the operation results as the output values of the neural network model 1300. For example, if the operation results of the one or more nodes of the last operation layer of the neural network layer 1320 are represented as $a_1, a_2, \ldots, a_M$, respectively, the output terminal 1330 may output $a_1, a_2, \ldots, a_M$ as the output values of the neural network model 1330. It should be noted that the number of the operation layer, the node and the parameters may be a predetermined number determined by the system 100, or may be adjusted according to different application scenarios by the user.

Figure 14A:
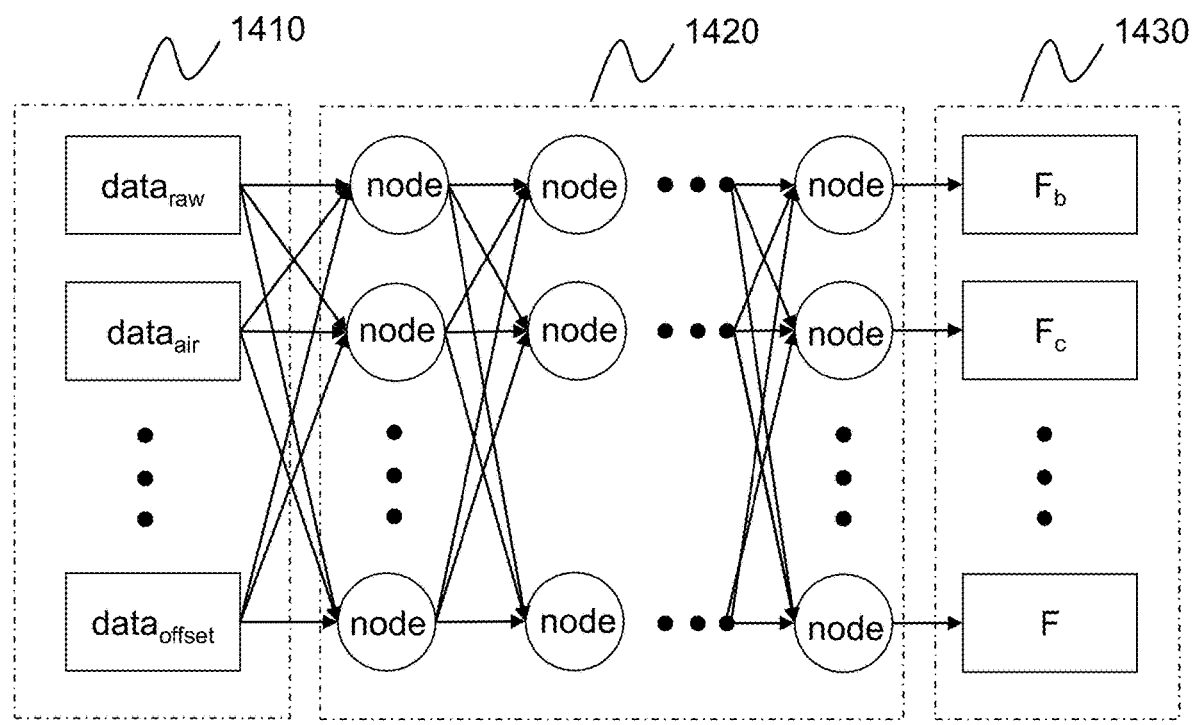
FIGS. 14A, 14B and 14C are schematic diagrams illustrating an exemplary neural network model according to some embodiments of the present disclosure.
Figure 14B:
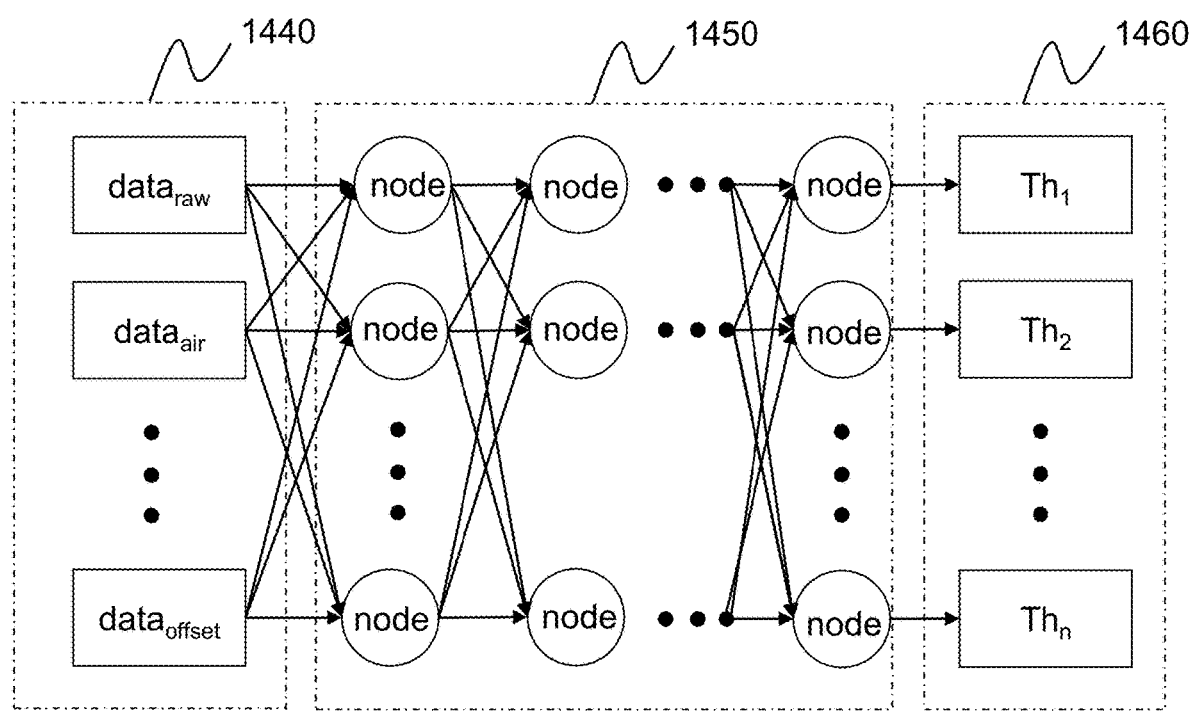
Figure 14C:
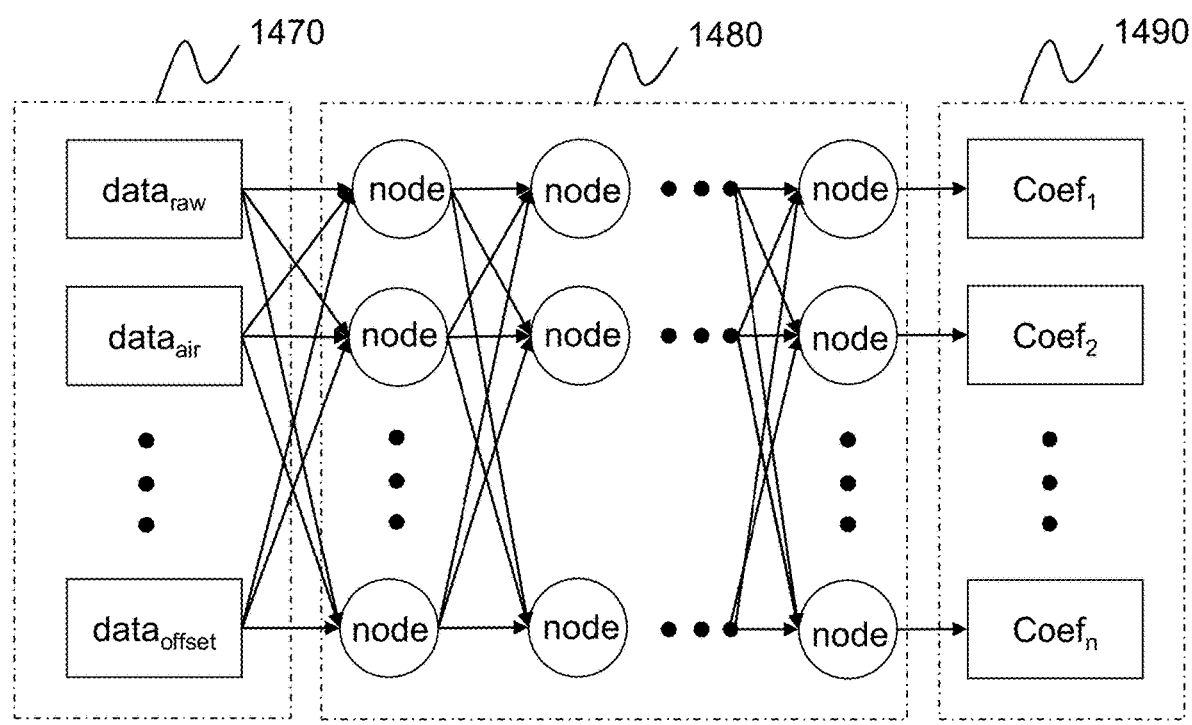

FIGS. 14A to 14C illustrate exemplary neural network models according to some embodiments of the present disclosure. The neural network model 1401, 1402, and/or 1403 may be generated through the process 1000 illustrated in FIG. 10. The neural network model 1401, 1402, and/or 1403 may be used to determine corresponding noise reduction parameters according to specific application scenario. As shown in FIG. 14A, the neural network model 1401 may include an input terminal 1410, a neural network layer 1420 and an output terminal 1430. The neural network model 1401 may be used to obtain the spectrum parameter of the noise of the raw projection data. In some embodiments, the input terminal 1410 may obtain input values and input the input values into the neural network layers 1420. The input value may include the raw projection data $data_{raw}$, the projection data generated by scanning air data$_{air}$, static drift of the detector data$_{offset}$, detector model, environmental information, detection parameters, or the like, or any combination thereof. The neural network model 1401 may output a set of spectrum parameters $\{F_i\}$ at the output terminal 1430 after operations conducted by the neural network layer 1420. $\{F_i\}$ may include cutoff frequency of the noise of the raw projection data, bandwidth of the noise of the raw projection data, or the like. The neural network layer 1420 may include one or more operation layers. Each operation layer may include one or more nodes. The neural network layer 1480 may be used to perform a calculation process (e.g., feature extraction, feature identification, or the like, or any combination) on the input values to obtain operation results. The output terminal 1430 may obtain the operation results of the neural network layer 1420 and designate the operation results as the output values of the neural network model 1401. For example, $\{F_i\}$ may be designated as the output values of the neural network model 1401.

As shown in FIG. 14-B, the neural network model 1402 may include an input terminal 1440, a neural network layer 1450 and an output terminal 1460. The neural network 1402 may be used to obtain the thresholds of each layer of the wavelet decomposition of the raw projection data. In some embodiments, the input terminal 1440 may obtain input values and input the input values into the neural network layer 1450. The input value may include the raw projection data data$_{raw}$, the projection data generated by scanning air data$_{air}$, static drift of the detector data$_{offset}$, detector model, environmental information, detection parameters, or the like, or any combination thereof. The neural network model 1402 may output a set of thresholds of the wavelet decomposition $\{Th_i\}$ at the output terminal 1460 after operations conducted by the neural network layer 1450, wherein i denotes the ith layer of the wavelet decomposition. $Th_i$ may represent the threshold of layer i of the wavelet decomposition. The neural network layer 1450 may include one or more operation layers. Each operation layer may include one or more nodes. The neural network layer 1480 may be used to perform a calculation process (e.g., feature extraction, feature identification, or the like, or any combination) on the input values to obtain operation results. The output terminal 1460 may obtain the operation results of the neural network layer 1450 and designate the operation results as the output values of the neural network model 1402. For example, $\{Th_i\}$ may be designated as the output values of the neural network model 1402.

As shown in FIG. 14C, the neural network model 1400-3 may include an input terminal 1470, a neural network layer 1480 and an output terminal 1490. The neural network 1400-3 may be used to obtain the regularization term coefficient of the total variation of the raw projection data. In some embodiments, the input terminal 1470 may obtain input values and input the input values into the neural network layer 1480. The input value may include the raw projection data data$_{raw}$, the projection data generated by scanning air data$_{air}$, static drift of the detector data$_{offset}$, detector model, environmental information, detection parameters, or the like, or any combination thereof. The neural network model 1400-3 may obtain a set of regularization term coefficients $\{Coef_n\}$ at the output terminal 1490 after operations conducted by the neural network layer 1450, wherein n denotes the nth regularization term coefficient. The neural network layer 1480 may include one or more operation layers. Each operation layer may include one or more nodes. The neural network layer 1480 may be used to perform a calculation process (e.g., feature extraction, feature identification, or the like, or any combination) on the input values to obtain operation results. The output terminal 1490 may obtain the operation results of the neural network layer 1480 and designate the operation results as the output values of the neural network model 1400-3. For example, $\{Coef_n\}$ may be designated as the output values of the neural network model 1400-3.

Figure 15:
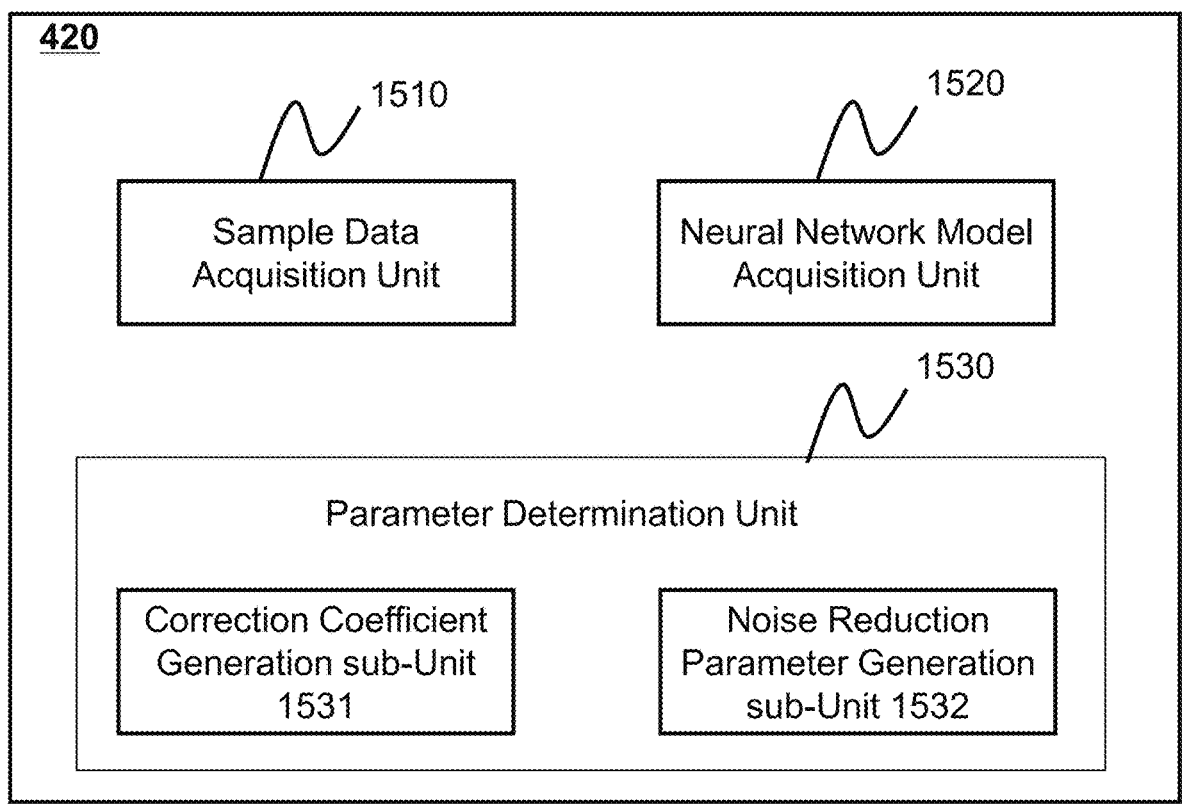
FIG. 15 is a block diagram illustrating an exemplary parameter determination module according to some embodiments of the present disclosure.

FIG. 15 is a block diagram illustrating an exemplary parameter determination module 420 according to some embodiments of the present disclosure. The parameter determination module 420 may include a sample data acquisition unit 1510, a neural network model acquisition unit 1520 and a parameter determination unit 1530. More or less components may be included in the processing engine without loss of generality. For example, two of the units may be combined into a single unit, or one of the sub-units may be divided into two or more units. In one implementation, one or more of the units may reside on a same or different computing devices (e.g., different server computers).

The sample data acquisition unit 1510 may be configured to obtain sample data. The sample data may include projection data, scanning parameter, or the like, or any combination thereof. For example, the sample data acquisition unit 1510 may obtain the raw projection data of the target from a detector. The sample data acquisition unit 1510 may also obtain projection data generated by scanning air. As another example, the sample data acquisition unit 1510 may obtain the scanning parameters such as the voltage of the X-ray tube and the electric current of the X-ray tube.

The neural network model acquisition unit 1520 may be configured to obtain a trained neural model generated by the neural network generation module 410. The trained neural model may be used to determine a parameter such as the correction coefficient or the noise reduction parameter. The neural network model acquisition unit 1520 may obtain the neural network model from the neural network generation module 410, or the storage 220 of the processing engine 140.

The parameter determination unit 1530 may be configured to determine a parameter. The parameter may include a correction coefficient, a noise reduction parameter, or the like. The parameter determination unit 1530 may determine the parameter based on the sample data and the trained neural network model. For example, the parameter determination unit 1530 may input the sample data into the trained neural network model to obtain the parameters after calculating and processing. The parameter determination unit 1530 may include a correction coefficient generation sub-unit 1531 and a noise reduction parameter generation sub-unit 1532. The correction coefficient generation sub-unit 1531 may be configured to determine the correction coefficient, and the noise reduction parameter generation sub-unit 1532 be configured to determine the noise reduction parameter.

Figure 16:
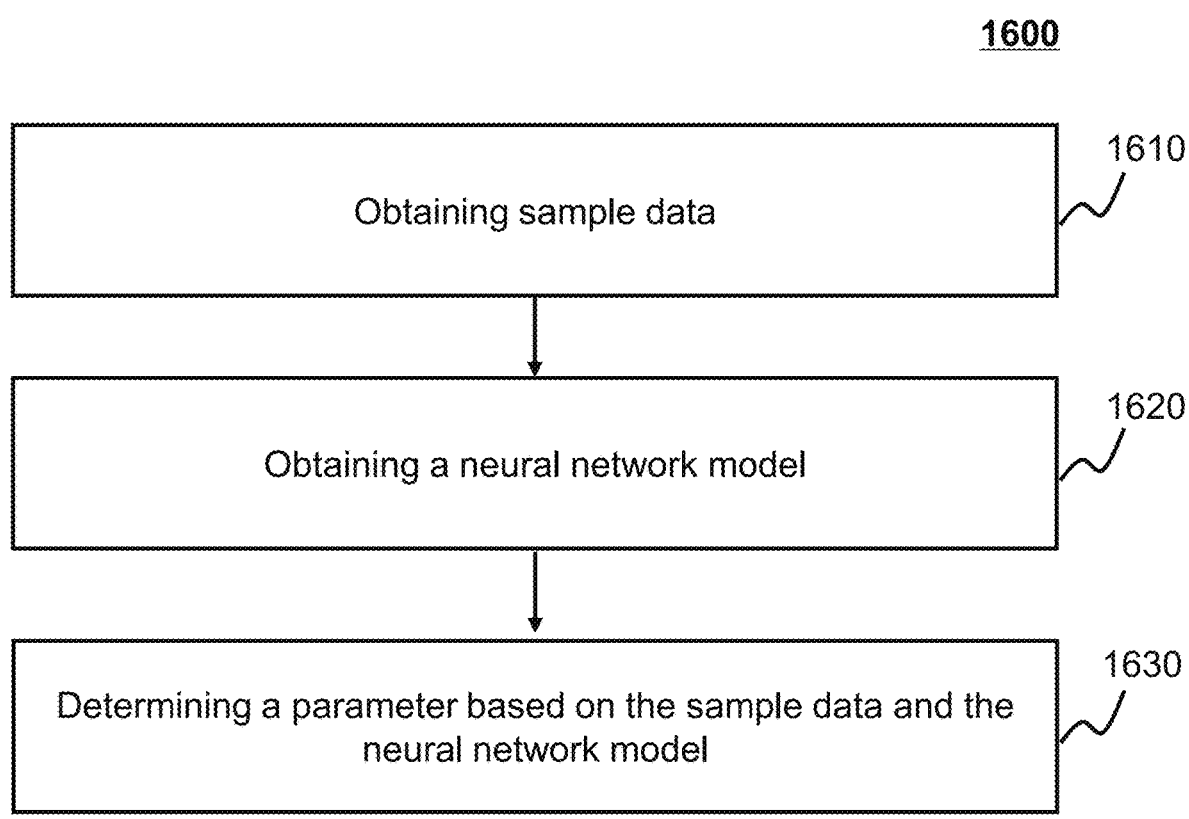
FIG. 16 is a flowchart illustrating an exemplary process for determining a parameter for medical data processing according to some embodiments of the present disclosure.

FIG. 16 is a flowchart illustrating an exemplary process 1600 for determining a parameter for medical data processing according to some embodiments of the present disclosure. The process 1600 may determine the parameter by employing the neural network model(s) illustrated in FIG. 12, FIG. 13, and/or FIG. 14. The generation of the neural network model(s) may be illustrated in FIGS. 7-10. Process 1600 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 1600 may be performed by or be implemented on the processing engine 140 of the medical imaging system 100.

In 1610, the sample data acquisition unit 1510 may obtain sample data.

In some embodiments, the sample data may include at least one of projection data or a scanning parameter. The projection data may be the raw projection data of a target obtained by a detector. The target may refer to a scanned object. For example, the target may include a human body, a part of human body (e.g., a head, a neck, a chest, a waist, etc.), an animal, a phantom, or the like, or any combination thereof. The scanning parameter may include a voltage of the X-ray tube, an electric current of the X-ray tube, scanning time, slice thickness, pitch, scanning volume, or the like. In some embodiments, the sample data may include first projection data. The first projection data may be generated by scanning air under the scanning parameter. In some embodiments, the projection data and the first projection data may be generated under the same scanning parameter.

In 1620, the neural network model acquisition unit 1520 may obtain a neural network model.

In some embodiments, the neural network model may be a trained neural network model. The description of the training process of the neural network model may be founded in FIG. 7 to FIG. 10, and may not be repeated here. In some embodiments, the neural network model acquisition unit 1520 may obtain the neural network model from the neural network generation module 410. The neural network model acquisition unit 1520 may also obtain the neural network model that has been already stored in the storage device 150 or the storage 220 of the processing engine 140.

In 1630, the parameter determination unit 1530 may determine a parameter based on the sample data and the neural network model.

In some embodiments, the parameter may include a correction coefficient, a noise reduction parameter, or the like. The correction coefficient may be a coefficient for correcting the erroneous data included in the projection data obtained under the scanning parameter. The noise reduction parameter may refer to parameter that may be used in a noise reduction process. For example, the noise reduction parameter may include spectrum parameter, threshold of the wavelet, regularization term coefficient, or the like, or any combination thereof. In some embodiments, via the parameter determination unit 1530, the sample data may be entered into the neural network model to obtain the parameter. For example, parameter determination unit 1530 may correct the projection data based on the correction coefficient to obtain corrected projection data and reconstruct a reconstruction image based on the corrected projection data. As another example, the parameter determination unit 1530 may perform a noise reduction operation on the projection data based on the noise reduction parameter.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, a step in which sample data may be stored may be added to the process 1600.

Figure 17:
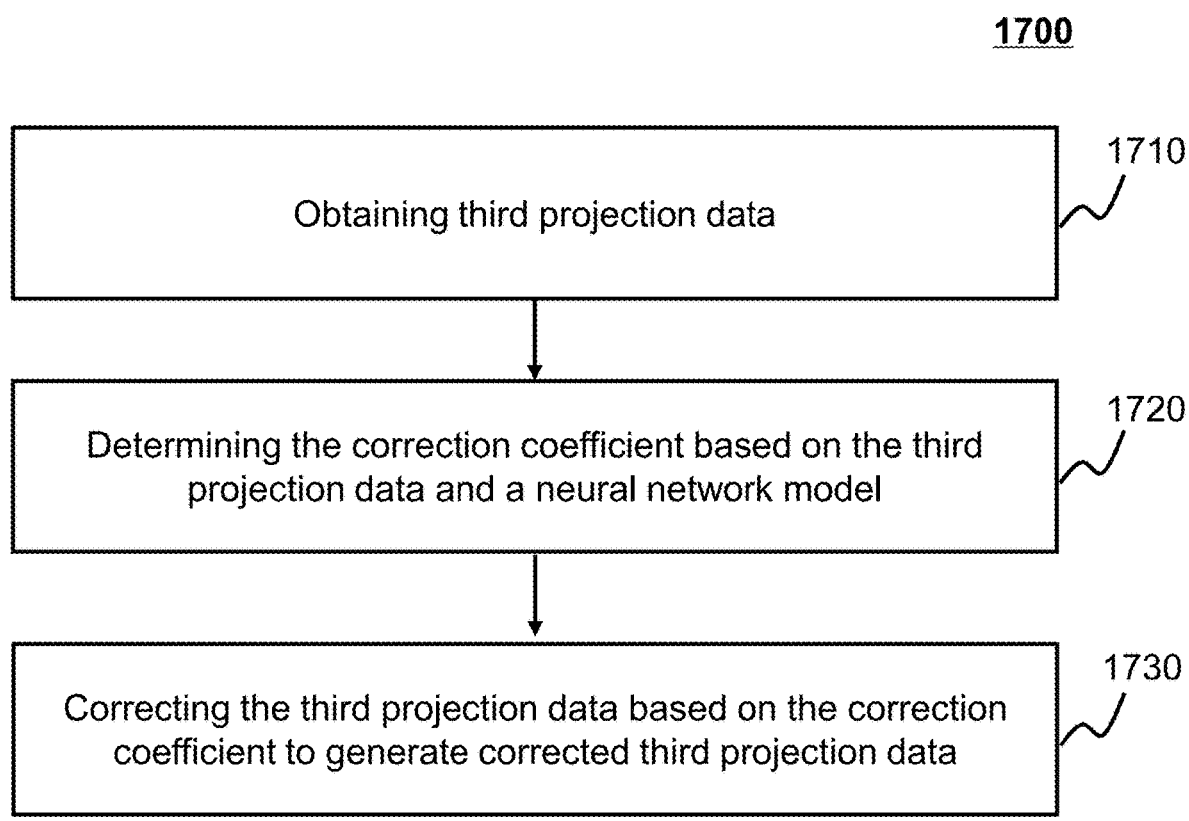
FIG. 17 is a flowchart illustrating an exemplary process for determining a parameter of projection data according to some embodiments of the present disclosure.

FIG. 17 is a flowchart illustrating an exemplary process 1700 for determining a parameter of projection data according to some embodiments of the present disclosure. The process 1600 may determine the parameter by employing the neural network model(s) illustrated in FIG. 12, which may be generated through the process 700 and process 800 illustrated respectively in FIG. 7 and FIG. 8. Process 1700 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 1700 may be performed by or be implemented on the processing engine 140 of the medical imaging system 100.

In 1710, the sample data acquisition unit 1510 may obtain third projection data.

In some embodiments, the third projection data may be the raw projection data of a detection target (or referred to as a subject). The detection target may include a human body, a part of human body (e.g., a head, a neck, a chest, a waist, etc.), an animal, a phantom, or the like, or any combination thereof. In some embodiments, the third projection data may be collected by the detector. The detector may detect the traversed radiation beams and generate the raw projection data of the detection target. In some embodiments, the third projection data may be generated under the scanning parameter. For example, the third projection data may be generated under the same scanning protocol as the first projection data and/or the second projection data.

In 1720, the correction coefficient generation sub-unit 1531 may determine the correction coefficient based on the third projection data and a neural network model.

In some embodiments, the correction coefficient may be a correction factor for reducing system error and/or random error. For example, the raw projection data of the detection target may include erroneous data because of the inconsistency of the detector units' response to the intensity of the ray field, the deviation of the detector installation position, or the signal crosstalk. The reconstruction image reconstructed based on the raw projection data may include components that does not exist in the detection target due to the erroneous data included in the raw projection data, for example, artifacts. Therefore, the correction coefficient may be used to correct or reduce the error of the raw projection data to obtain corrected projection data of a detection target. In some embodiments, the neural network model may be a trained neural network model for obtaining correction coefficient. For example, the neural network model may be obtained in process 700 or process 800. The neural network model acquisition unit 1520 may obtain the trained neural network model after the execution of process 700/800.

In some embodiments, the parameter of the trained neural network may be the relevant parameter of the detector, for example, the correction coefficient. In some embodiments, the correction coefficient may be determined according to equation (5):

$$[a_i, b_i, c_i, \ldots ] = f(\text{raw}_m, \text{raw}_{ideal}, kV, \ldots) \qquad (5)$$

wherein $a_i$, $b_i$, $c_i$ denote the correction coefficient, f denotes the trained neural network model, $\text{raw}_m$ denotes the raw projection data (e.g., the first projection data) of the phantom, $\text{raw}_{ideal}$ denotes the reference projection data (e.g., the second projection data) of the phantom, kV denotes the scanning condition (e.g., scanning parameter). After trained with a plurality of training samples (e.g., the raw projection data obtained under different scanning conditions and the reference projection data by processing the raw projection data), the neural network model may output the correction coefficient.

In 1730, the processor 210 may correct the third projection data based on the correction coefficient to generate corrected third projection data.

In some embodiments, the corrected third projection data may be projection data with less erroneous data or without erroneous data. For example, the reconstruction image reconstructed based on the corrected third projection data may do not have artifacts. In some embodiments, the processor 210 may construct a correction model based on the correction coefficient. The correction model may be used to generate corrected projection data. For example, the raw projection data may be input directly into the correction model to obtain the corrected projection data. In some embodiments, the correction model may be represented according to equation (6):

$$y = \Sigma_{i=0}^{M} a_i x^i + \Sigma_{i=0}^{N} b_i (dx)^i + \Sigma_{i=0}^{P} c_i (d^2 x)^i + \quad (6)$$

Wherein y denotes the corrected projection data, x denotes the raw projection data, $a_i$, $b_i$, $c_i$ denote the correction coefficient, dx denotes the first derivative of the detector response, $d^2 x$ denotes the second derivative of the detector response, M, N, P denote the correction order which generally do not exceed three according to the correction effect confirmation. In some embodiments, the first derivative in response to the detector dx may be designated as data correction based on the position of the detector. The second derivative response to the detector $d^2 x$ may be designated as data correction based on the interference signal crosstalk. As shown in equation (6), the correction model may correct the influence of detector property, detector position and signal crosstalk on the raw projection data to obtain the corrected projection data y. The processor 210 may obtain a better correction effect of the artifacts based on the multivariate correction method described above.

In some embodiments, the processor 210 may reconstruct an image based on the corrected third projection data. The image may be a reconstruction image without artifacts. In some embodiments, the method for image reconstruction may include a filter back projection algorithm, an algebraic reconstruction algorithm, a local reconstruction algorithm, or the like. The processor 210 may send the reconstruction image to the user of the terminal 130 via the network 120 for subsequent operations.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, a step in which third projection data may be stored may be added to the process 1700.

Figure 18:
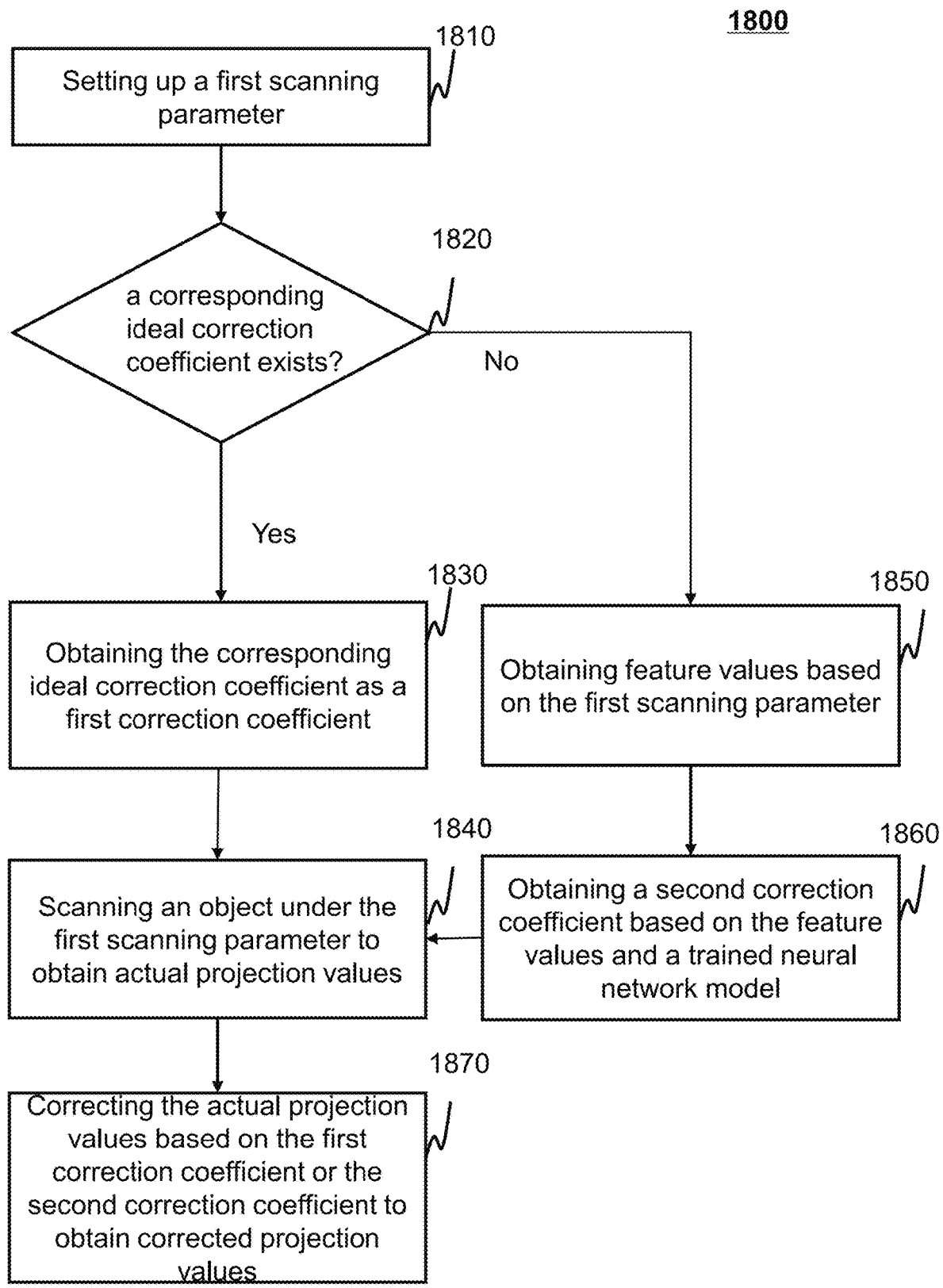
FIG. 18 is a flowchart illustrating an exemplary process for determining a parameter of projection data according to some embodiments of the present disclosure.

FIG. 18 is a flowchart illustrating an exemplary process 1800 for determining a parameter of projection data according to some embodiments of the present disclosure. Process 1800 may determine the parameter by employing the neural network model illustrated in FIG. 13, which may be generated through the process 900 illustrated in FIG. 9. Process 1800 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 1700 may be performed by or be implemented on the processing engine 140 of the medical imaging system 100.

In 1810, the processor 210 may set up a first scanning parameter. In some embodiments, the first scanning parameter may include a voltage of the X-ray tube, an electric current of the X-ray tube, scanning time, slice thickness, pitch, scanning volume, or the like. In some embodiments, the processor 210 may set up the first scanning parameter based on actual application scenario automatically. In some embodiments, the user of the terminal 130 may send a parameter setting instruction to the processor 210 via the network 120. And the processor 210 may set up the first scanning parameter based on the parameter setting instruction.

In 1820, the processor 210 may determine whether the first scanning parameter has a corresponding reference correction coefficient.

In some embodiments, the corresponding reference correction coefficient may refer to a coefficient that may be used to correct the erroneous data included in the projection data which is obtained under the first scanning parameter. The reference correction coefficients for different scanning parameters may be obtained in advance. Each reference correction coefficient may correspond to a specific scanning parameter. The reference correction coefficients and the corresponding specific scanning parameters may be stored in the storage 220 of the processing engine 140, or may be stored in the storage device 150. The reference correction coefficient may be an ideal correction coefficient. The ideal correction coefficient may be obtained by calculating projection data of standard phantom after scanning. Detailed description of the standard phantom may be illustrated in FIG. 9 and the description thereof. In some embodiments, the reference correction coefficients may be obtained by a conventional correction method, or may be obtained by physical simulation. In some embodiments, after the first scanning parameter is determined, the processor 210 may conduct a retrieve process in the storage 220 or device 150 to confirm whether there exists a specific scanning parameter the same as the first scanning parameter and a corresponding reference correction coefficient. If the specific scanning parameter and the corresponding reference correction coefficient already exit in the storage 220 or 150, the process 1800 may proceed to 1830.

In 1830, the processor 210 may obtain the corresponding reference correction coefficient as a first correction coefficient. The first correction coefficient may be the same as the corresponding reference correction coefficient and may be used to correct the projection data obtained under the first projection parameter.

In 1840, the medical imaging system 100 may scan an object under the first scanning parameter to obtain actual projection values. In some embodiments, the object may include a human body, a part of human body (e.g., a head, a neck, a chest, a waist, etc.), an animal, a phantom, or the like, or any combination thereof. In some embodiments, the actual projection values may be collected by the detector. The detector may send the actual projection values to the processor 210 via the network 120.

Return to 1820, if no specific scanning parameter the same as the first scanning parameter and the corresponding reference correction coefficient exist in the storage 220 or 150, the process 1800 may proceed to 1850.

In 1850, the sample data acquisition unit 1510 may obtain feature values based on the first scanning parameter.

In some embodiments, the feature values may include at least one of the first scanning parameter and the first projection data. The first projection data may refer to projection data obtained by scanning the air under the first scanning parameter. In some embodiments, the feature values may include the first projection data. In some embodiments, the feature values may include the first scanning parameter. In some embodiments, the feature values may include the first scanning parameter and the first projection data. In some embodiments, the processor 210 may send the feature values to the storage 220 of the processing engine 140 and/or the storage device 150 via the network 120.

In 1860, the correction coefficient generation sub-unit 1531 may obtain a second correction coefficient based on the feature values and a trained neural network model.

In some embodiments, the second correction coefficient may be a coefficient for correcting the erroneous data included in the actual projection data obtained under the first projection parameter. The trained neural network model may refer to a neural network model that is used to obtain correction coefficient. The description of training the neural network may be founded in elsewhere in the present disclosure (FIG. 9). The neural network model acquisition unit 1520 may obtain the trained neural network model after the execution of process 900. In some embodiments, the correction coefficient generation sub-unit 1531 may input the feature values into the trained neural network model. In some embodiments, the correction coefficient generation sub-unit 1531 may perform the calculation process (e.g., feature extraction, feature identification, etc.) on the feature values and obtain operation results. In some embodiments, the correction coefficient generation sub-unit 1531 rather than the neural network layer 1320 may perform the calculation process. Detailed description may be found in FIG. 13 and the description thereof. The output of the trained neural network model may be the second correction coefficient. After obtaining the second correction coefficient, the processor 210 may send the second correction coefficient to the storage 220 of the processing engine 140 and/or the storage device 150 via the network 120. The medical imaging system 100 may update the storage data by adding the corresponding reference correction coefficient (e.g., the second correction coefficient) to the first scanning parameter.

In 1870, the processor 210 may correct the actual projection values based on the first correction coefficient or the second correction coefficient to obtain corrected projection values.

In some embodiments, the corrected projection values may be projection values with few erroneous values or without erroneous values. In some embodiments, the corrected projection values may be obtained according to equation (7):

$$y = \sum_{i=0}^{j} a_i x^i \quad (7).$$

In equation (7), y denotes the corrected projection values, x denotes the actual projection values, j denotes the configurable correction order, j may be a numerical value, such as 3 or 4. In some embodiments, j may be determined by the user. $a_i$ denotes the correction coefficient, for example, the first correction coefficient or the second correction coefficient. In some embodiments, referring to 1820, if the judgment is "Yes", the actual projection values may be corrected based on the first correction coefficient in 1870. If the judgment is "No", the actual projection values may be corrected based on the second correction coefficient in 1870.

In some embodiments, the corrected projection values may be used to reconstruct an image, for example, a reconstruction image, using an image reconstruction method such as filter back projection algorithm, algebraic reconstruction algorithm or local reconstruction algorithm. The processor 210 may send the reconstruction image to the user of the terminal 130 via the network 120 for subsequent operations.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 1820 and 1830 may be unnecessary and may be omitted. The obtaining of correction coefficient may be performed directly based on operation 1850. As another example, operation 1840 may be performed prior to operation 1850.

Figure 19:
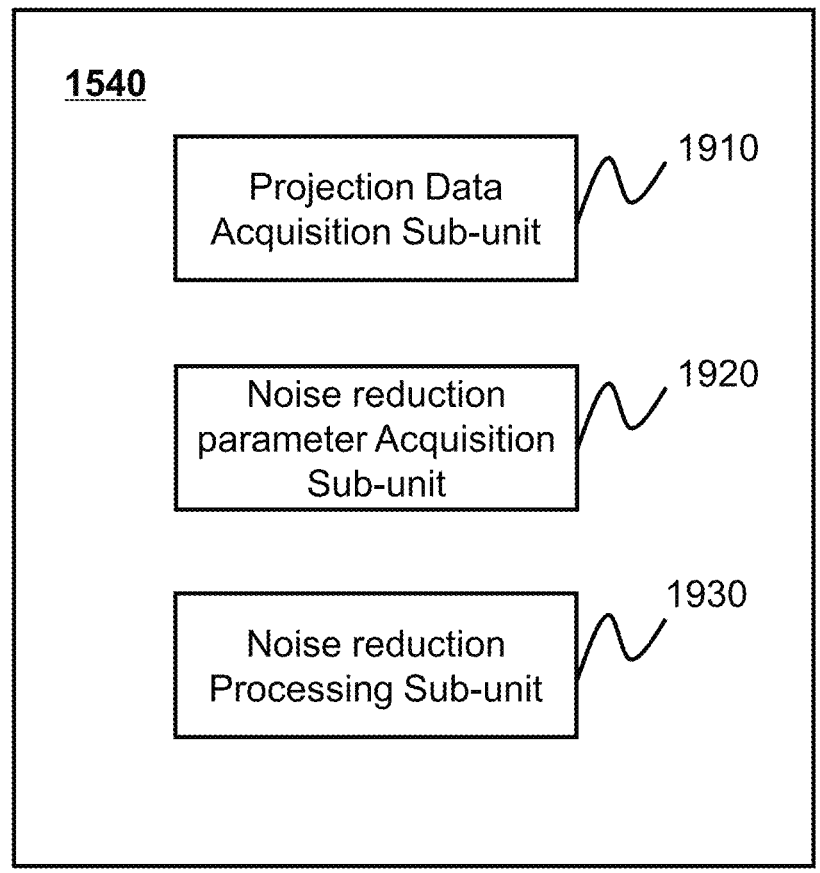
FIG. 19 is a block diagram illustrating an exemplary noise reduction processing unit according to some embodiments of the present disclosure.

FIG. 19 is a block diagram illustrating an exemplary noise reduction processing unit 1540 according to some embodiments of the present disclosure. In some embodiments, the noise reduction processing unit 1540 may be a part of the parameter determination module 420. The noise reduction processing unit 1540 may include a projection data acquisition sub-unit 1910, a noise reduction parameter acquisition sub-unit 1920 and a noise reduction processing sub-unit 1930. More or less components may be included in the processing engine without loss of generality. For example, two of the sub-units may be combined into a single sub-unit, or one of the sub-units may be divided into two or more sub-units. In one implementation, one or more of the sub-units may reside on a same or different computing devices (e.g., different server computers).

The projection data acquisition sub-unit 1910 may be configured to obtain projection data. In some embodiments, the projection data may be the raw projection data of a detection target, for example, a human body, an animal, a phantom, or the like. The projection data acquisition sub-unit 1910 may obtain projection data from the detector after the detector detects the radiation beams and generates the raw projection data of the detection target.

The noise reduction parameter acquisition sub-unit 1920 may be configured to determine a noise reduction parameter of the projection data. For example, the noise reduction parameter acquisition sub-unit 1920 may obtain a trained neural network model to determine the noise reduction parameter of the projection data. The noise reduction parameter may include spectrum parameter, threshold of the wavelet, regularization term coefficient, or the like, or any combination thereof. The noise reduction parameter acquisition sub-unit 1920 may determine the noise reduction parameter based on different type of trained neural network and the raw projection data of the detection target.

The noise reduction processing sub-unit 1930 may be configured to perform a noise reduction operation on the projection data based on the noise reduction parameter to obtain corrected projection data. For example, the noise reduction processing sub-unit 1930 may perform the noise reduction operation on the raw projection data by using low-pass filter. As another example, the noise reduction processing sub-unit 1930 may perform the noise reduction operation on the raw projection data by wavelet decomposition. As still another example, the noise reduction processing sub-unit 1930 may perform the noise reduction operation on the raw projection data by total variation.

It should be noted that the above description of the neural network generation module 410 is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure. For example, the noise reduction parameter acquisition sub-unit 1920 and the projection data acquisition sub-unit 1910 may be integrated into a single unit.

Figure 20:
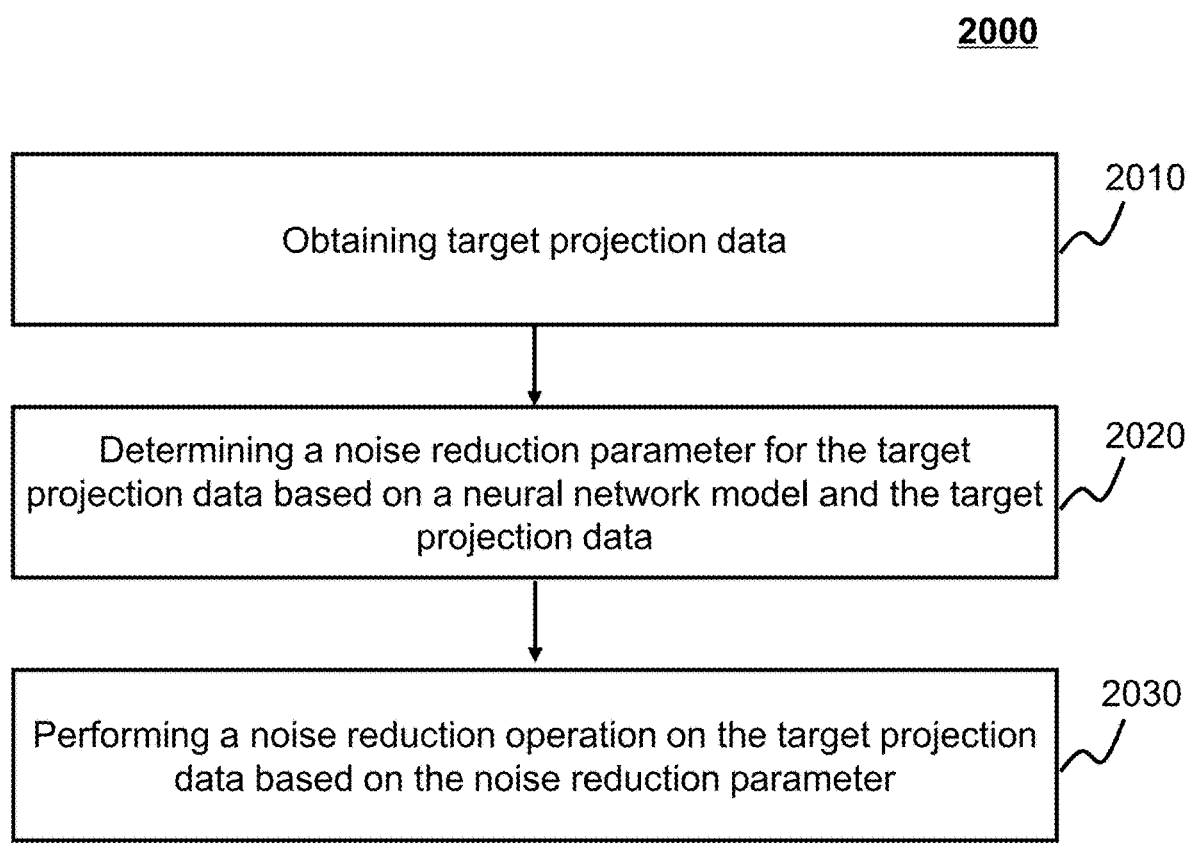
FIG. 20 is a flowchart illustrating an exemplary process for reducing noise on projection data according to some embodiments of the present disclosure.

FIG. 20 is a flowchart illustrating an exemplary process 2000 for reducing noise on projection data according to some embodiments of the present disclosure. Process 2000 may be performed by processing logic that comprises hardware (e.g., circuitry, dedicated logic, programmable logic, microcode, etc.), software (e.g., instructions run on a processing device to perform hardware simulation), or a combination thereof. In some embodiments, process 2000 may be performed by or be implemented on the processing engine 140 of the medical imaging system 100.

In 2010, the projection data acquisition sub-unit 1910 may obtain target projection data.

In some embodiments, the target projection data may be the raw projection data obtained by the detector by scanning a detection target. For example, the detection target may include a human body, a part of human body (e.g., a head, a neck, a chest, a waist, etc.), an animal, a phantom, or the like, or any combination thereof. The detector may detect the radiation beams and generate the target projection data of the detection target, and may send the actual projection values to the processor 210 via the network 120. In some embodiments, the target projection data may include noise following a spatial distribution. In some embodiments, the noise may include Gaussian noise, white noise, salt and pepper noise, shot noise, quantization noise, anisotropic noise, periodic noise, or the like, or any combination thereof.

In 2020, the noise reduction parameter generation sub-unit 1532 may determine a noise reduction parameter for the target projection data based on a neural network model and the target projection data.

In some embodiments, the noise reduction parameter may refer to parameter that may be used in a noise reduction process. For example, the noise reduction parameter may include spectrum parameter, threshold of the wavelet, regularization term coefficient, or the like, or any combination thereof. In some embodiments, the neural network model may be a trained neural network model for obtaining the noise reduction parameter. For example, the neural network model may be obtained in process 1000. The noise reduction parameter acquisition sub-unit 1920 may obtain the trained neural network model the after the execution of process 1000.

In some embodiments, the noise reduction parameter acquisition sub-unit 1920 may determine the spectrum parameter of the noise distribution of the target projection data based on the trained neural network model (e.g., as shown in FIG. 14A) and the target projection data. The spectrum parameter of the noise distribution may include the cutoff frequency of the noise and/or the bandwidth of the noise. In some embodiments, the spectrum parameter of the noise distribution may be determined according to equation (7):

$$[F_c, F_b] = f_1(\text{data}_{raw}, \text{data}_{air}, \text{data}_{offset}) \quad (7).$$

In the equation (7), $\text{data}_{raw}$ denotes the target projection data, $\text{data}_{air}$ denotes the detector response data generated by scanning air, $\text{data}_{offset}$ denotes the static drift of the detector, $F_c$ denotes the cutoff frequency of the noise, $F_b$ denotes the bandwidth of the noise, $f_1$ denotes a function expression of the trained neural network model. In some embodiments, the input of the trained neural network model may also include detector model, environmental information, detection parameters, or the like. The trained neural network model may perform a calculation process (e.g., feature extraction, feature identification, or the like, or any combination) on the input values to obtain the spectrum parameter of the noise distribution of the target projection data.

In some embodiments, the noise reduction parameter acquisition sub-unit 1920 may determine the thresholds of each layer of the wavelet decomposition of the target projection data based on the trained neural network model (e.g., as shown in FIG. 14B) and the target projection data. The thresholds may refer to a high frequency coefficient corresponding to each layer. In some embodiments, the spectrum parameter of the noise distribution may be determined according to equation (8):

$$[Th_1, Th_2, \ldots, Th_n] = f_2(\text{data}_{raw}, \text{data}_{air}, \text{data}_{offset}) \quad (8)$$

Wherein $\text{data}_{raw}$ denotes the target projection data, $\text{data}_{air}$ denotes the detector response data generated by scanning air, $\text{data}_{offset}$ denotes the static drift of the detector, $Th_n$ denotes the threshold for a layer of the wavelet decomposition of the target projection data, $f_2$ denotes a function expression of the trained neural network model. In some embodiments, the input of the trained neural network model may also include detector model, environmental information, detection parameters, or the like. The trained neural network model may perform a calculation process (e.g., feature extraction, feature identification, or the like, or any combination) on the input values to obtain the thresholds of each layer of the wavelet decomposition of the target projection data.

In some embodiments, the noise reduction parameter acquisition sub-unit 1920 may determine regularization term coefficient of the total variation of minimize data of the raw projection data based on the trained neural network model (e.g., as shown in FIG. 14C) and the target projection data. In some embodiments, the spectrum parameter of the noise distribution may be determined according to equation (9):

$$[Coef_1, Coef_2, \ldots, Coef_n] = f_3(\text{data}_{raw}, \text{data}_{air}, \text{data}_{offset}) \quad (9)$$

Wherein $\text{data}_{raw}$ denotes the target projection data, $\text{data}_{air}$ denotes the detector response data generated by scanning air, $\text{data}_{offset}$ denotes the static drift of the detector, $Coef_n$ denotes the regularization term coefficient, $f_3$ denotes a function expression of the trained neural network model. In some embodiments, the input of the trained neural network model may also include detector model, environmental information, detection parameters, or the like. The trained neural network model may perform a calculation process (e.g., feature extraction, feature identification, or the like, or any combination) on the input values to obtain the regularization term coefficients of the total variation of the raw projection data.

In 2030, the noise reduction processing sub-unit 1930 may perform a noise reduction operation on the target projection data based on the noise reduction parameter.

In some embodiments, the noise reduction operation may be performed on the target projection data by using low-pass filter. The low-pass filter may allow the low frequency signals of the projection data to pass through. The signals with a frequency higher than the cutoff frequency may be weakened or decreased by the low-pass filter. Therefore, the noise of the target projection data may be reduced by the low-pass filter because the noise is generally a high frequency signal. In some embodiments, the cutoff frequency may be obtained from the spectrum parameter. The spectrum parameter may include cutoff frequency and/or bandwidth of the noise.

In some embodiments, the noise reduction operation may be performed on the target projection data by wavelet decomposition. An N-layer wavelet decomposition may be performed on the target projection data. The N-layer wavelet decomposition may refer to a sequential decomposition process. For example, $1^{st}$-layer wavelet decomposition may be performed on the target projection data to obtain three $1^{st}$-layer high frequency components and one $1^{st}$-layer low frequency component. Then, a $2^{nd}$-layer wavelet decomposition may be performed on the $1^{st}$-layer low frequency component to obtain three $2^{nd}$-layer high frequency components and one $2^{nd}$-layer low frequency component. The low frequency components obtained in each layer wavelet decomposition may be continuously decomposed. The $N^{th}$-layer wavelet decomposition may be performed on the $N-1^{th}$-layer low frequency component to obtain three $N^{th}$-layer high frequency components and one $N^{th}$-layer low frequency component. The three high frequency components obtained in each layer decomposition may correspond to the horizontal direction, the vertical direction and the diagonal direction, respectively. Each high frequency component may be processed by performing a threshold quantization. The threshold quantization may include hard threshold quantization and soft threshold quantization. The hard threshold quantization may refer to that when the high frequency components of the wavelet decomposition are greater than a selected threshold, the high frequency components may be directly determined as the quantized high frequency components. The soft threshold quantization may refer to that when the high frequency components of the wavelet decomposition are greater than a selected threshold, the high frequency components may shrink to zero according to a certain fixed quantity and the shrunken high frequency components may be determined as the quantized high frequency components. The selected threshold may be the thresholds of each layer of the wavelet decomposition determined in operation 2020. The fixed quantity may be a preset value stored in the system 100, or may be set by the user of the terminal 130.

In some embodiments, the noise reduction operation may be performed on the target projection data by total variation. Via the total variation, the purpose of noise reduction may be achieved by minimizing energy function. The regularization term coefficients determined in operation 2020 may be used to construct regularization terms to solve the minimization energy function of the total variation. For example, the energy function of the target projection data may be represented according to equation (10):

$$TV[u(x,y)] = \iint_\Omega |\nabla u(x,y)| dxdy \qquad (10)$$

Wherein $TV[u(x,y)]$ denotes the target projection data of the total variation, $\nabla u(x,y)$ denotes the gradient of the target projection data, $|\nabla u(x,y)|$ denotes the norm of $\nabla u(x,y)$, $\Omega$ denotes the area of the target projection data. The total variation noise reduction energy functional may be according to equation (11):

$$E = \int_\Omega \frac{1}{2}(u - u_0)^2 + \lambda * TV(u) \qquad (11)$$

Wherein $\lambda$ denotes the first regularization term coefficient. The first regularization term coefficient may be a positive constant and may be used to balance the noise reduction and smoothing of the target projection data. In order to minimize the energy function, an Euler-Lagrange function may be used to determine the minimum value of the energy function. The Euler-Lagrange function may be represented according to equation (12):

$$\frac{\partial u}{\partial t} = -\nabla\left(\frac{\nabla u}{|\nabla u|_\beta}\right) + \lambda(u - u_0) = 0 \qquad (12)$$

Wherein t denotes time scale factor, $\nabla = (\partial/\partial x, \partial/\partial y)$, denotes gradient operator, $|\nabla u|_\beta = \sqrt{|\nabla u| + \beta^2}$ denotes regularization term, $\beta$ denotes the second regularization term coefficient. In some embodiments, the regularization term coefficient $Coef_1$ determined in operation 2020 may be $\lambda$, and the regularization term coefficient $Coef_2$ determined in operation 2020 may be $\beta$. The minimum value of the energy function of the total variation may be determined based on the regularization term coefficients and the Euler-Lagrange function.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, a step in which the target projection data and/or the image data may be stored may be added to the process 2000.

Figures 21A, 21B:
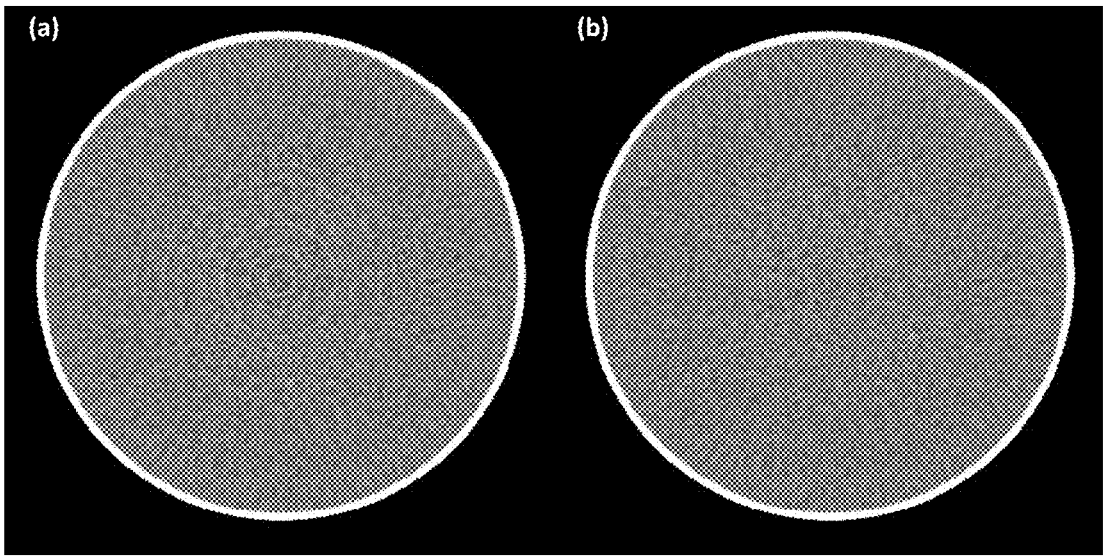
FIGS. 21-A to 21-B illustrate exemplary reconstruction images of a phantom according to some embodiments of the present disclosure.
Figure 22A:
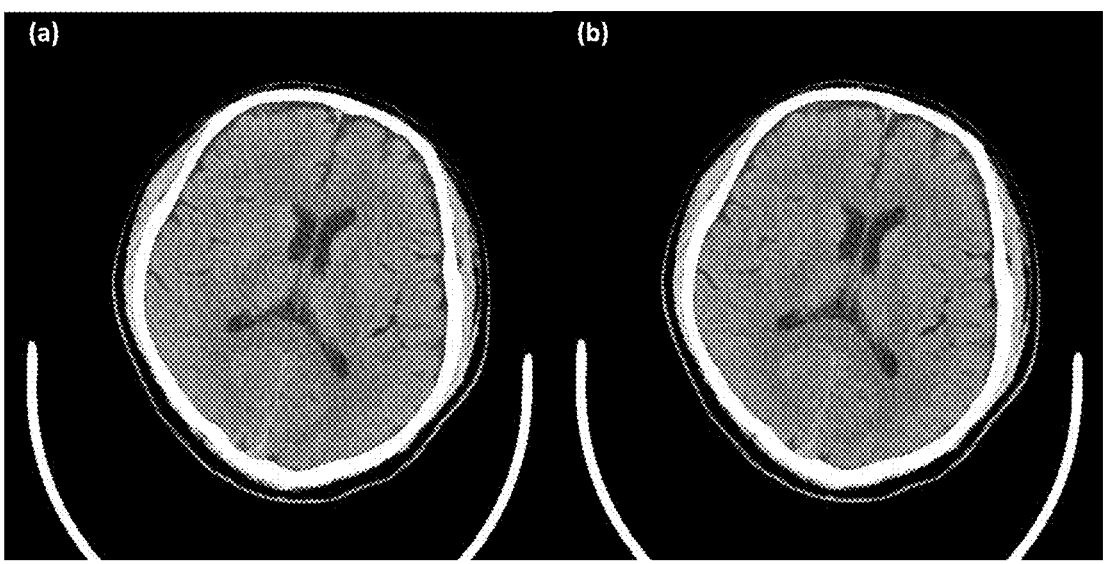
FIGS. 22-A to 22-B illustrate exemplary reconstruction images of human body according to some embodiments of the present disclosure.

FIG. 21A illustrate a reconstruction image reconstructed based on raw projection data of the phantom, FIG. 22A illustrate a reconstruction image reconstructed based on raw projection data of human body. As shown in FIG. 21A and FIG. 22A, a plurality of artifact (e.g., ring artifacts) may be founded in the reconstruction images. Refer to FIG. 21B and FIG. 22B, FIG. 21B and FIG. 22B illustrate the reconstruction images reconstructed based on corrected projection data that is corrected by the above described methods. Obviously, after projection data correcting, the artifacts may not exist in the reconstruction image. The correction coefficients and noise reduction parameter obtained by trained neural network model may be used to correct the erroneous data of human projection data with a high efficiency.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one computing device, each of which has at least one processor and storage for determining a parameter for medical data processing, the method comprising:
   obtaining sample data, wherein the sample data comprises at least one of projection data or a scanning parameter;
   obtaining a first neural network model;
   inputting the sample data into the first neural network;
   obtaining an output of the first nueral network generated based on the sample data; and
   designating the output of the first neural network as the parameter, the parameter comprising at least one of a correction coefficient or a noise reduction parameter.

2. The method of claim 1, wherein the correction coefficient is configured to correct an artifact relating to the projection data.

3. The method of claim 2, where in the obtaining a first neural network model comprises:
generating an initial neural network model;
obtaining first projection data of a subject corresponding to a plurality of scanning parameters, wherein the first projection data of the subject is generated by scanning the subject with a scanner, and the plurality of scanning parameters relating to at least one of the scanner or the subject;
generating second projection data of the subject based on the first projection data of the subject; and
training the initial neural network model with the first projection data and the second projection data to obtain the first neural network model.

4. The method of claim 3, wherein the subject comprises a phantom.

5. The method of claim 4, wherein the generating second projection data of the subject based on the first projection data of the subject comprises:
reconstructing a first image of the subject from the first projection data of the subject;
smoothing the first image of the subject to generate a second image of the subject; and
projecting the second image of the subject to generate the second projection data of the subject.

6. The method of claim 3, wherein the generating second projection data of the subject based on the first projection data of the subject comprises:
smoothing the first projection data of the subject to generate the second projection data.

7. The method of claim 3, wherein the generating second projection data of the subject based on the first projection data of the subject comprises:
reconstructing a first image of the subject from the first projection data of the subject;
modelling the subject according to the first image; and
calculating analytic equations of an X-ray transmission process to obtain the second projection data of the subject.

8. The method of claim 3, wherein the plurality of scanning parameters comprise at least one of a tube voltage of the scanner or a tube current of the scanner.

9. The method of claim 2, wherein the sample data comprises third projection data, and the determining the parameter based on the sample data and the first neural network model comprises:
determining the correction coefficient based on the third projection data and the first neural network model, the third projection data being generated under the scanning parameter;
correcting the third projection data based on the correction coefficient to generate corrected third projection data; and
reconstructing an image based on the corrected third projection data.

10. The method of claim 9, wherein the correcting the third projection data based on the correction coefficient comprises:
constructing a correction model based on the correction coefficient; and
generating the corrected third projection data based on the third projection data and the correction model.

11. The method of claim 1, wherein the correction coefficient is configured to correct errors induced by a detector that collects the projection data.

12. The method of claim 11, wherein the sample data comprises first projection data being generated by scanning air under the scanning parameter, and the determining a parameter based on the sample data and the first neural network model comprises:
determining the correction coefficient based on the first projection data and the first neural network model.

13. The method of claim 11, wherein the obtaining a first neural network model comprises:
generating an initial neural network model;
obtaining a plurality of training samples, each of the plurality of training samples comprising at least one of a second scanning parameter or second projection data, the second projection data being generated by scanning air under the second scanning parameter; and
training the initial neural network model with the at least one of the second scanning parameter or the second projection data to obtain the first neural network model.

14. The method of claim 1, wherein the obtaining a first neural network model comprises:
generating an initial neural network model;
obtaining training projection data and noise distribution of the training projection data; and
training the initial neural network model with the training projection data and the noise distribution of the training projection data to obtain the first neural network model.

15. The method of claim 1, further comprising:
performing a noise reduction operation on the projection data based on the parameter, the parameter being a noise reduction parameter.

16. A system for determining a parameter for medical data processing, comprising:
at least one storage medium including a set of instructions; and
at least one processor configured to communicate with the at least one storage medium, wherein when executing the set of instructions, the at least one processor is directed to:
obtain sample data, wherein the sample data comprises at least one of projection data or a scanning parameter;
obtain a first neural network model;
inputting the sample data into the first neural network;
obtaining an output of the first nueral network generated based on the sample data; and
designating the output of the first neural network as the parameter, the parameter comprising at least one of a correction coefficient or a noise reduction parameter.

17. The method of claim 16, wherein the correction coefficient is configured to correct an artifact relating to the projection data.

18. The system of claim 17, wherein the at least one processor is further configured to:
generate an initial neural network model;
obtain first projection data of a subject corresponding to a plurality of scanning parameters, wherein the first projection data of the subject is generated by scanning the subject with a scanner, and the plurality of scanning parameters relating to at least one of the scanner or the subject;
generate second projection data of the subject based on the first projection data of the subject; and
train the initial neural network model with the first projection data and the second projection data to obtain the first neural network model.

19. The system of claim 18, wherein the subject comprises a phantom.

20. The system of claim 19, wherein the at least one processor is further configured to:
    reconstruct a first image of the subject from the first projection data of the subject;
    smooth the first image of the subject to generate a second image of the subject; and
    project the second image of the subject to generate the second projection data of the subject.

21. The method of claim 18, wherein to generate the second projection data of the subject based on the first projection data of the subject, the at least one processor is configured to:
    reconstruct a first image of the subject from the first projection data of the subject;
    model the subject according to the first image; and
    calculate analytic equations of an X-ray transmission process to obtain the second projection data of the subject.

22. The method of claim 18, wherein the plurality of scanning parameters comprises at least one of a tube voltage of the scanner or a tube current of the scanner.

23. The method of claim 16, wherein the correction coefficient is configured to correct errors induced by a detector that collects the projection data.

24. The method of claim 23, wherein the sample data comprises first projection data being generated by scanning air under the scanning parameter, and the at least one processor is further configured to:
    determine the correction coefficient based on the first projection data and the first neural network model.

25. A non-transitory computer readable medium including executable instructions that, when executed by at least one processor, cause the at least one processor to effectuate a method comprising:
    obtaining sample data, wherein the sample data comprises at least one of projection data or a scanning parameter;
    obtaining a first neural network model;
    inputting the sample data into the first neural network;
    obtaining an output of the first nueral network generated based on the sample data; and
    designating the output of the first neural network as the parameter, the parameter comprising at least one of a correction coefficient or a noise reduction parameter.

* * * * *